US009023386B2

(12) United States Patent
Benita et al.

(10) Patent No.: US 9,023,386 B2
(45) Date of Patent: May 5, 2015

(54) MICROSPHERES COMPRISING NANOCAPSULES CONTAINING A LIPOPHILIC DRUG

(75) Inventors: Shimon Benita, Mevasseret Zion (IL); Alona Rom, Mazkeret Batiya (IL); Taher Nasser, Tur'an Village (IL)

(73) Assignee: Yissum Research Development Company of the Hebrew University of Jerusalem, Jerusalem (IS)

( * ) Notice: Subject to any disclaimer, the term of this patent is extended or adjusted under 35 U.S.C. 154(b) by 651 days.

(21) Appl. No.: 12/219,540

(22) Filed: Jul. 23, 2008

(65) Prior Publication Data

US 2009/0011009 A1 Jan. 8, 2009

Related U.S. Application Data

(63) Continuation-in-part of application No. PCT/IL2007/000084, filed on Jan. 23, 2007.
(60) Provisional application No. 60/760,935, filed on Jan. 23, 2006.

(51) Int. Cl.
| | |
|---|---|
| *A61K 9/48* | (2006.01) |
| *A61K 9/51* | (2006.01) |
| *A61K 9/66* | (2006.01) |
| *A61K 9/50* | (2006.01) |
| *A61K 31/436* | (2006.01) |
| *A61K 31/4523* | (2006.01) |
| *A61K 31/7048* | (2006.01) |
| *A61K 9/00* | (2006.01) |

(52) U.S. Cl.
CPC ............ *A61K 9/5089* (2013.01); *A61K 9/0019* (2013.01); *A61K 9/0095* (2013.01); *A61K 9/5042* (2013.01); *A61K 9/5138* (2013.01); *A61K 9/5161* (2013.01); *A61K 9/5192* (2013.01); *A61K 31/436* (2013.01); *A61K 31/4523* (2013.01); *A61K 31/7048* (2013.01)

(58) Field of Classification Search
USPC ...................................................... 424/452
See application file for complete search history.

(56) References Cited

U.S. PATENT DOCUMENTS

| 5,965,160 | A | 10/1999 | Benita et al. |
| 6,589,562 | B1 | 7/2003 | Shefer et al. |
| 6,884,433 | B2 | 4/2005 | Yamashita et al. |
| 2003/0147965 | A1 | 8/2003 | Bassett et al. |
| 2004/0109894 | A1 | 6/2004 | Shefer et al. |
| 2005/0013828 | A1* | 1/2005 | George et al. .............. 424/189.1 |

FOREIGN PATENT DOCUMENTS

EP 0 480 729 A1 4/1992

OTHER PUBLICATIONS

Nishioka, et al., "The effect of various surfactants on the release rate of propranolol hydrochloride from hydroxypropylmethylcellulose (HPMC)—Eudragit matrices", 2002, European Journal of Pharmaceutics and Biopharmaceutics, vol. 54, pp. 349-356.*
Holm, et al., "Examination of oral absorption and lymphatic transport of halofantrine in a triple—cannulated canine model after administration in self-microemulsifying drug delivery systems (SMEDDS) containing structured triglycerides", European Journal of Pharmaceutical Sciences, vol. 20, pp. 91-97, (2003).
O'Driscoll, "Mini review: Lipid-based formulations for intestinal lymphatic delivery", European Journal of Pharmaceutical Sciences, vol. 15, pp. 405-415, (2002).
Hauss, et al., "Lipid-Based Delivery Systems for Improving the Bioavailability and Lymphatic Transport of a Poorly Water-Soluble LTB4 Inhibitor", Journal of Pharmaceutical Sciences, vol. 87, No. 2, pp. 164-169, (1998).
Cook, et al., "Novel sustained release microspheres for pulmonary drug delivery", Journal of Controlled Release, vol. 104, pp. 79-90, (2005).
Khoo, et al., "Formulation design and bioavailability assessment of lipidic self-emulsifying formulations of halofantrine", International Journal of Pharmaceutics, vol. 167, pp. 155-164, (1998).
Christensen, et al., "Preparation of redispersible dry emulsions by spray drying", International Journal of Pharmaceuticals, vol. 212, pp. 187-194, (2001).
Honbo, et al., "The Oral Dosage Form of FK-506", Transplantation Proceedings, vol. 19, No. 5, suppl. 6, pp. 17-22, (1987).
Shimada, et al., "Lowered Blood Concentration of Tacrolimus and its Recovery with Changes in Expression of CYP3A and P-Glycoprotein After High-Dose Steroid Therapy", Transplantation, vol. 74, No. 10, pp. 1419-1424, (2002).
Uno, et al., "Pharmacokinetic Advantages of a Newly Developed Tacrolimus Oil-in-Water-Type Emulsion via the Enteral Route", Lipids, vol. 34, No. 3, pp. 249-254, (1999).
Manjunath, et al., "Pharmacokinetics, tissue distribution and bioavailability of clozapine solid lipid nanoparticles after intravenous and intraduodenal admistration", Journal of Controlled Release, vol. 107, pp. 215-228, (2005).
Swartz, "The physiology of the lymphatic system", Advanced Drug Delivery Reviews, vol. 50, pp. 3-20, (2001).
Jani, et al., "The Uptake and Translocation of Latex Nanospheres and Microspheres after Oral Administration to Rats", J. Pharm. Pharmacol., vol. 41, pp. 809-812, (1989).
Delie, "Evaluation of nano- and microparticle uptake by the gastrointestinal tract", Advanced Drug Delivery Reviews, vol. 34, pp. 221-233, (1998). Nishioka, et al., "Lymphatic targeting with nanoparticulate system", Advanced Drug Delivery Reviews, vol. 47, pp. 55-64, (2001).
Schaffazick, et al., "Development of Nanocapsule Suspensions and Nanocapsule Spray-Dried Powders Containing Melatonin", J. Braz. Chem. Soc., vol. 17, No. 3, pp. 562-569, (2006).
Fessi, et al., "Nanocapsule formation by interfacial polymer deposition following solvent displacement", International Journal of Pharmaceutics, vol. 55, pp. R1-R4, (1989).
Notification of Transmittal of the International Search Report and the Written Opinion of the International Searching Authority (PCT/ISA/220), 2 pages; International Search Report (PCT/ISA/210), 5 pages; Written Opinion of the International Searching Authority (PCT/ISA/237), 10 pages; of the corresponding PCT International Application No. PCT/IL2007/000084, mailed on Oct. 8, 2007.

* cited by examiner

*Primary Examiner* — Michael B Pallay
(74) *Attorney, Agent, or Firm* — Vorys, Sater, Seymour and Pease LLP; Susanne M. Hopkins; Ari G. Zytcer

(57) ABSTRACT

The present invention provides microspheres comprising a plurality of nanocapsules accommodated in a gel forming polymer, the plurality of nanocapsules comprising an oil core carrying a non hydrophilic active agent and a shell of polymeric coating. The invention also provides a method for preparing the microspheres of the invention, pharmaceutical compositions comprising the same as well as methods of use of the microspheres, specifically, in therapeutic, cosmetic and diagnostic applications.

36 Claims, 19 Drawing Sheets

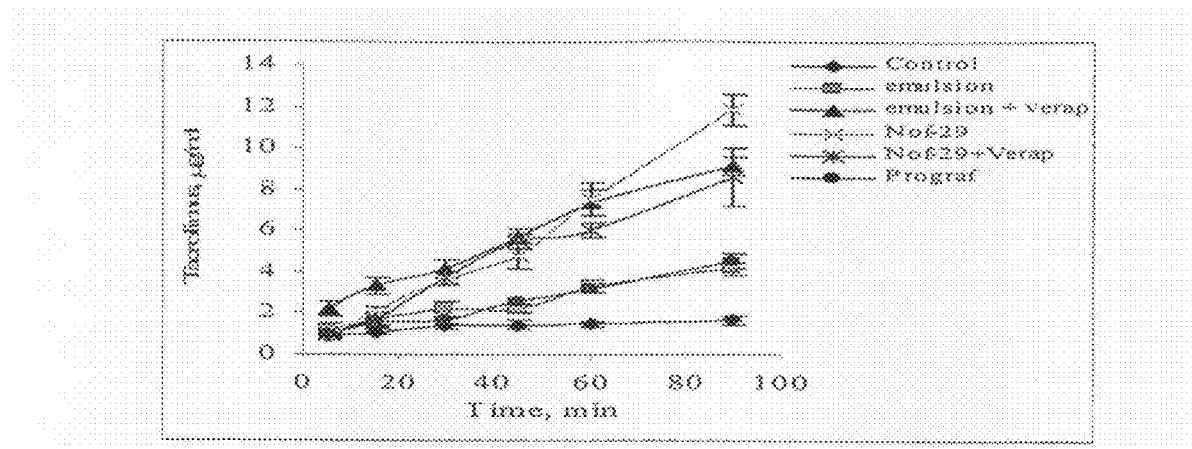
Figure 24
Figure 25A
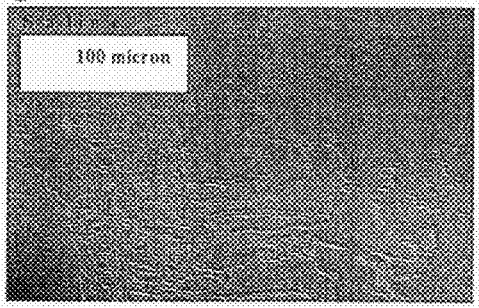
Figure 25B
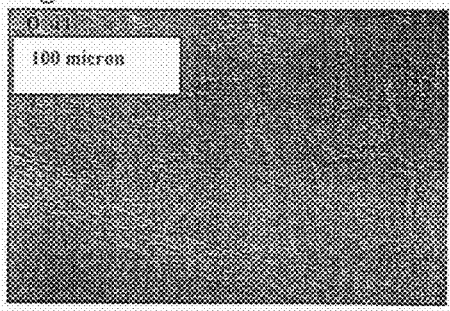
Figure 25C
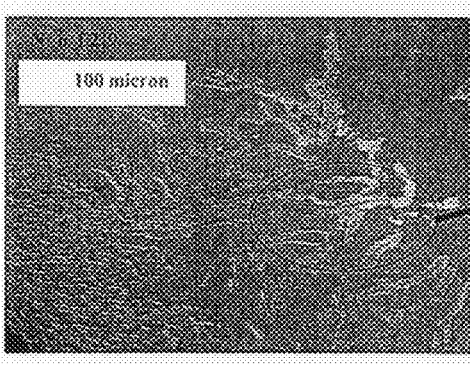
Figure 25D

MICROSPHERES COMPRISING NANOCAPSULES CONTAINING A LIPOPHILIC DRUG

This application is a Continuation-in-Part of International Application No.: PCT/IL2007/000084, filed on Jan. 23, 2007, which claims the benefit of U.S. Provisional Patent Application Ser. No. 60/760,935, filed on Jan. 23, 2006, the entire content of which is hereby incorporated by reference in its entirety.

FIELD OF THE INVENTION

This invention relates to delivery systems for active agents, preferably for oral intake.

PRIOR ART

The following is a list of prior art which is considered to be pertinent for describing the state of the art in the field of the invention. Acknowledgement of these references herein will at times be made by indicating their number within brackets from the list below.
1. Holm R, Porter C J H, Edwards Ga, Mullertz A, Kristensen H G and Charman W N. Examination of oral absorption and lymphatic transport of halofantrine in a triple-cannulated canine model after administration in self-microemulsifying drug delivery system (SMEDDS) containing structured triglycerides. Eur. J. Pharm. Sci. 20:91-97 (2003).
2. O'Driscoll C M. Lipid-based formulations for intestinal lymphatic delivery. Eur J Pharm Sci. 15:405-15. (2002).
3. Tamura S, Ohike A, Ibuki R, Amidon G L, Yamashita S. Tacrolimus is a class II low-solubility high-permeability drug: the effect of P-glycoprotein efflux on regional permeability of tacrolimus in rats. J Pharm Sci. 91:719-29. (2002).
4. Hauss D J, Fogal S E, Ficorilli J V, Price C A, Roy T, Jayaraj A A, Keirns J J. Lipid-based delivery systems for improving the bioavailability and lymphatic transport of a poorly water-soluble LTB4 inhibitor. J. Pharm. Sci. 87:164-9 (1998).
5. EP 480,729, Haibung L, Soonhong Y. Microencapsulation for controlled oral drug delivery system.
6. U.S. Pat. No. 5,965,160, Benita S, et al. Self-emulsifiable formulation producing an oil-in-water emulsion.
7. Cook R O, Pannu R K, Kellaway I W. Novel sustained release microspheres for pulmonary drug delivery. J Control Release. 104:79-90. (2005).
8. Khoo S M, Humberstone. A J, Porter C J H, Edwards G A, and Charman W N. Formulation design and bioavailability assessment of lipidic self-emulsifying formulations of halofantrine. Int. J. Pharm. 167:155-164 (1998).
9. Christensen, K. L., et al. *Preparation of redisperible dry emulsions by spray drying*. Intl. J. Pharm. 212:187-194 (2001).
10. Honbo T, Kobayashi M, Hane K, Hata T, Ueda Y. The oral dosage form of FK-506. Transplant. Proc. 19 (Suppl 6): 17-22 (1987).
11. Shimada T, Terada A, Yokogawa K, Kaneko H, Nomura M, Kaji K, Kaneko S, Kobayashi K, Miyamoto K. Lowered blood concentration of tacrolimus and its recovery with changes in expression of CYP3A and P-glycoprotein after high-dose steroid therapy. Transplantation. 74:1419-24 (2002).
12. Uno T, Kazui T, Suzuki Y, Hashimoto H, Suzuki K, Muhammad B A. Pharmacokinetic advantages of a newly developed tacrolimus oil-in-water-type emulsion via the enteral route. Lipids. 34: 249-54 (1999).
13. U.S. Pat. No. 6,884,433, Yamashita K., et al. Sustained release formulation containing tacrolimus.
14. Manjunath et al., Pharmacokinetics, tissue distribution and bioavailability of clozapine solid lipid nanoparticles after intravenous and intraduodenal administration, Journal of Controlled Release 107 (2005) 215-228.
15. Swartz M. A. The physiology of the lymphatic system, Adv. Drug Deliv. Rev. 50 (2001) 3-20.
16. Jani, P. U., et al., Uptake and translocation of latex nanospheres and microspheres after oral administration to rats, J. Pharm. Pharmacol. 41 (1989) 809-812.
17. Florence D. Evaluation of nano- and microparticles uptake by the gastrointestinal tract, Adv. Drug Deliv. Rev. 34 (1998) 221-233.
18. Nishioka Y., et al., Lymphatic targeting with nanoparticulate system, Adv. Drug Deliv. Rev. 47 (2001) 55-64.
19. US 2003/0147965, Bassett M, Jacob J. and Enscore D. Methods and products useful in the formation and isolation of microparticles.

BACKGROUND OF THE INVENTION

Recent advances in drug design and delivery have led to the development of an increasing number of highly lipophilic drug molecules which may be substrates for intestinal lymphatic transport. However, these drugs exhibit poor oral bioavailability owing either to low dissolution, P-glycoprotein efflux or CYP3A4 metabolism prior to absorption in the gastrointestinal tract, thus limiting their availability.

The adequate pharmaceutical formulation of such drugs remains a challenge which is not yet fully solved. It is well known that lipids are capable of enhancing lymphatic transport of hydrophobic drugs, thereby reducing drug clearance resulting from hepatic first-pass metabolism. This improves drug absorption, bioavailability profiles, activity and lowers toxicity. The commercial success of self-emulsifying drug delivery system (SEDDS) formulations such as Neoral® (cyclosporin A), Norvir® (ritonavir) and Fortovase® (saquinavir) has raised the interest in such promising emulsion-based delivery systems to improve the oral bioavailability of lipophilic drugs (1). It is believed that SEDDS which spread out as fine oil droplets in the GI tract enhance the bioavailability by promoting lymphatic transport of the lipophilic drugs. Indeed, it was recently proved that the extent of lymphatic transport via the thoracic duct was 27.4% of the halofantrine dose for the animals dosed with the structured triglyceride SMEDDS (1). In addition, it was recently reported that under certain circumstances, the lymphatics may provide the primary route of drug absorption and lead to drug concentration in the lymph some 5-10,000 times higher than in systemic plasma (2). Recent advances in drug design and delivery, have also led to the development of an increasing number of highly lipophilic drug molecules which may be substrates for intestinal lymphatic transport. There is an increase in interest in the role of the lymphatic in determining drug absorption and bioavailability profiles, activity and toxicity. For example, an increasing body of evidence has shown that certain lipids are capable of inhibiting both presystemic drug metabolism and p-glycoprotein-mediated (Pgp-mediated) drug efflux by the gut wall (3)

EP 480,729 (4) discloses a microencapsulation method for oral administration of a drug dispersed in an oil droplet. The oil droplet is encapsulated using a polysaccharide which has metal-chelating capacity and a water-soluble polymer. The encapsulation protects the drug from release in the stomach, while providing rapid release in the small intestine. Since the drug in the oil droplet is preferentially absorbed by lymphatic absorption, it is protected from degradation by hepatic first-pass metabolism.

U.S. Pat. No. 5,965,160 (5) discloses a self-emulsifying oily formulation (SEOF) which may contain a hydrophobic drug, comprising an oil component and a surfactant. The SEOF is characterized in that the oil component comprises an oily carrier and a cationic lipid and, optionally, a lipophilic oily fatty alcohol. The oil-in-water emulsion which forms upon mixture of the SEOF with an aqueous solution has oily droplets which are positively charged.

Cook, R. O., et al. (6) describes a process for generating sustained release particles for pulmonary drug delivery. According to this process nanoparticles of the hydrophilic, ionised drug terbutaline sulphate are entrapped within hydrophobic microspheres using a spray-drying approach.

Khoo, S M, et al. (7) disclose dispersed lipid-based formulations for the oral delivery of lipophilic drugs such as Halofantrine. Both a lipidic self-emulsifying drug delivery system (SEDDS) and a self-microemulsifying drug delivery system (SMEDDS) are described. The systems comprise a triglyceride, mon-/diglyceride, nonionic surfactant, a hydrophilic phase and the drug substance. Optimised formulations were medium-chain triglyceride (MCT) SEEDS and SMEDDS, and a long-chain triglyceride (LCT) SMEDDS.

Holm, R, et al. (1) describe a SMEDDS containing triglycerides with different combinations of medium-chain and long-chain fatty acids, where the different fatty acids on the glycerol backbone exhibit different metabolic fates.

Christensen, K. L., et al. (9) describe the preparation of stable dry emulsions which are able to reform the original o/w emulsion by reconstitution in water. The dry emulsions contained a water-soluble polymer such as hydroxypropylmethylcellulose (HPMC), methylcellulose or povidone, as solid carrier, and fractionated coconut oil. The liquid o/w emulsions were spray dried in a laboratory spray drier. The droplet size of the reconstituted emulsion was approximately 1 µm. Tacrolimus (Prograf®) is a macrolide immunosuppressive agent (MW of 804) that is derived from the fungus *Streptomyces tsukubaensis*, and has been shown to be effective in graft rejection prophylaxis and in the management of acute and steroid- or cyclosporine-resistant transplant rejection. tacrolimus is considered as an alternative to cyclosporine immunosuppression and was shown to be 10-100 times more potent than cyclosporine. tacrolimus was approved by the FDA for the prevention of liver transplant rejection in April, 1994.

Like cyclosporine, pharmacokinetic parameters of tacrolimus show high inter- and intra-individual variability and both drugs have a narrow therapeutics index, necessitating therapeutics whole-blood drug monitoring to optimize treatment. Absorption and oral bioavailability (10-25%) of tacrolimus are poor, with reduced rate and extent of absorption in the presence of food. Tacrolimus is rapidly, albeit incompletely, absorbed in the gastrointestinal tract. Tacrolimus peak concentration whole blood ($C_{max}$) is attained approximately 1-2 hours after oral administration. Due to the low aqueous solubility, tissue distribution of tacrolimus following oral or parenteral therapy is extensive (10). Tacrolimus is mainly bound to albumin and alpha$_1$-acid glycoprotein. Erythrocytes bind 75-80% of the drug resulting in whole blood concentrations that are 10- to 30 times higher than plasma concentrations (10). Tacrolimus is almost completely metabolized prior to elimination. Metabolism is via cytochrome P450 (CYP) 3A4 isoenzymes in the liver and, to a lesser extent, CYP3A4 isoenzymes and P-glycoprotein in the intestinal mucosa. The elimination half-life of tacrolimus in liver transplant patients is about 12 hours. Less than 1% of the dose is excreted unchanged in the urine. The P-glycoprotein efflux of tacrolimus from intestinal cells back into the gut lumen allows for CYP3A4 metabolism prior to absorption, thus limiting tacrolimus availability (11). When tacrolimus is administered with inhibitors of both CYP3A4 and P-glycoprotein (e.g., diltiazem, erythromycin, or ketoconazole), oral bioavailability enhancement is observed. There is a need for oral bioavailability enhancement of tacrolimus by drug delivery.

Uno, T, et al. (12) describe an oil-in-water (o/w) emulsion of the drug tacrolimus based on oleic acid. The mean diameters of the o/w emulsion droplets were 0.47 µm. The disclosed formulation exhibited bioavailability, pharmacokinetic advantages and potential usefulness of the emulsion as a carrier for tacrolimus enteral route compared to standard marketed formulation.

U.S. Pat. No. 6,884,433 (13) describe sustained release formulation containing tacrolimus as well as other macrolide compounds. The sustained release formulation disclosed therein comprises a solid dispersion of tacrolimus or its hydrates, in a mixture comprising a water soluble polymer (such as hydroxypropylmethylcellulose) and a water insoluble polymer (such as ethylcellulose) and an excipient (such as lactose). In the dispersion, the particle size is equal to or less than 250 µm.

In order to overcome first pass metabolism and thus low oral bioavailability intestinal lymphatic transport of drugs can be therefore, exploited. As previously mentioned, highly lipophilic compounds reach systemic circulation via the lymphatics. The majority of fatty acids, with chain lengths of 14 and above, were found to be recovered in thoracic lymph (14).

In addition, the size is one of the most important determinants of lymphatic uptake. Optimum size for lymphatic uptake was found to be between 10 and 100 nm (15). However, uptake is more selective and slower as the particle size increases. Larger particles may be retained for longer periods in the Peyer's patches, while smaller particles are transported to the thoracic duct (16). Oral administration of polymeric nano- and microparticles are taken up by lymphatic system through M cells of Peyer's patches of intestine was evidenced and proved in the literature (17). Nanoparticles coated with hydrophobic polymers tend to be easily captured by lymphatic cells in the body (18).

Another method for encapsulation of drugs into microparticles was described by Bassett et al. (19). The method involves phase inversion by dissolving the drug and a first polymer in a solvent and adding to the thus formed mixture a second polymer dissolved in a "non-solvent" which leads to the spontaneous formation of polymer coated micro or nanoparticles.

SUMMARY OF THE INVENTION

It is an object of the present invention to provide a system for the delivery of various active agents which are non-hydrophilic in character within a living body.

Thus, in one aspect of the invention, there is provided microspheres comprising a plurality of nanocapsules accommodated in a gel-forming polymer, the nanocapsules comprising an oil core carrying a non hydrophilic active agent and a shell of polymeric coating.

The invention also provides a method of preparing microspheres comprising a plurality of nanocapsules accommodated in a gel-forming polymer, the nanocapsules comprising an oil core carrying a non hydrophilic active agent and a shell of polymeric coating, the method comprising:

(a) providing an organic phase comprising oil, a water miscible organic solvent, a non-hydrophilic active agent dissolved in the solvent and a polymer or combination of polymers for coating said oil core;
(b) slowly adding water to said organic phase to obtain an emulsion;
(c) continuously adding water to the emulsion to induce phase inversion of the said emulsion thereby obtaining an oil in water (o/w) emulsion;
(d) mixing said o/w emulsion with a gel forming polymer or a combination of gel forming polymers;
(e) removing said organic solvent and water to obtain said microspheres.

The invention also provides pharmaceutical compositions comprising as the active component microspheres comprising a plurality of nanocapsules accommodated in a gel-forming polymer, the nanocapsules comprising an oil core carrying a non hydrophilic active agent and a shell of polymeric coating.

Further, the invention provides a method of increasing bioavailability of an active agent a human subject's body, the method comprises administering to said subject microspheres comprising a plurality of nanocapsules accommodated in a gel-forming polymer, the nanocapsules comprising an oil core carrying a non hydrophilic active agent and a shell of polymeric coating.

Yet further, the invention provides a method of treating a subject for a pathological condition which require for said treatment an effective amount of a an active agent with the subject's blood, the method comprises administering to said subject microspheres comprising a plurality of nanocapsules accommodated in a gel-forming polymer, the nanocapsules comprising an oil core carrying a non hydrophilic active agent and a shell of polymeric coating.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIG. 1B is an enlargement of FIG. 1A.

FIG. 3B is an enlargement of FIG. 3A.

(FIG. 23A) or the influence of the blank drug delivery system on tacrolimus residue in Hanks buffer (pH 7.4) following 60 min incubation in Caco-2 cell monolayer and respective tacrolimus uptake following washing and cell lysis (SDS 1%) of various formulations containing 25 µg/ml tacrolimus. The concentration of verapamil when appropriate was 150 µg/ml. N=4 in all the experiments (FIG. 23B).

FIG. 24 is a graph showing mucosal to serosal passage of tacrolimus across small intestine in various formulations. The concentration of verapamil when appropriate was 150 µg/ml. Data represents mean±S.D., N=4.

FIG. 25A-25D are fluorescence photomicrographs of histological section of rat jejunum 30 minutes following oral gavage of saline (FIG. 25A), oil phase core (FIG. 25B) and microencapsulated nanocapsule formulation NOF-29 loaded with Nile red marker 91 mg/ml oil phase (FIGS. 25C, 25D). Nile red nanocapsules at the jejunum lumen and adhering nanocapsules to the enterocyte membrane and in the cytoplasm of the enterocytes (FIGS. 25C, 25D).

DETAILED DESCRIPTION OF THE INVENTION

Figure 1A:
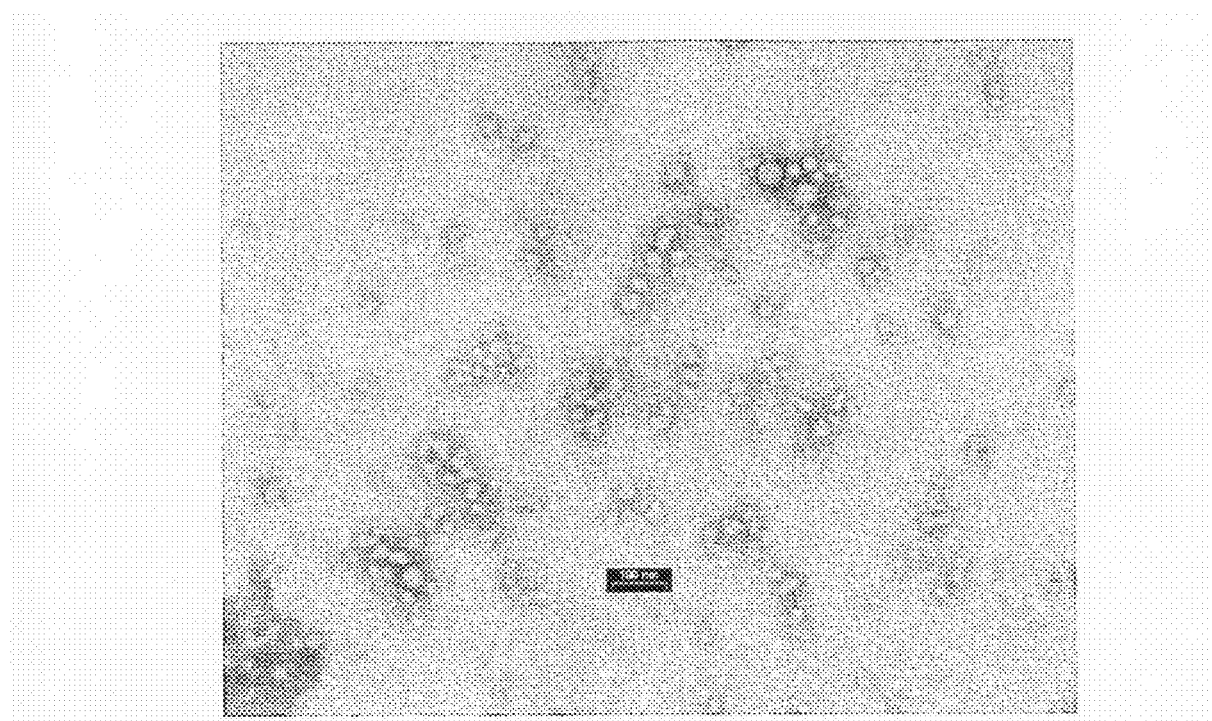
FIGS. 1A-1B are TEM micrographs of the nanocapsule formulation No. 29 before adding the hydroxypropylmethylcellulose solution. The volume ratio of the acetonic solution to the water solution is 100:75. Bar represents 100 nm in size.

The present invention is based on the finding that the formation of microspheres comprising a plurality of tiny oil droplets coated by a polymer blend, the plurality of polymer coated oil droplets being further accommodated in a gel forming polymer, significantly increased blood levels of lipophilic drugs dissolved in the oil core. These "double coated oil droplets" have led to the understanding that microspheres accommodating a plurality of nanocapsules may serve as a delivery vehicle for various active agents which non-hydrophilic in nature.

Thus, in accordance with one embodiment, there are provided microspheres comprising a plurality of nanocapsules accommodated in a gel-forming polymer, the nanocapsules comprising an oil core carrying a non hydrophilic active agent and a shell of polymeric coating.

The term "microspheres" which may be used interchangeably with the terms "microparticles" broadly defines micron- or submicron-scale particles which are typically composed of solid or semi-solid materials and capable of carrying and releasing a drug or any other active agent-holding nanocapsule enclosed therein. The microspheres in accordance with the invention are more or less of a spherical structure comprised of aggregates of nanocapsules incorporating (e.g. embedding, encapsulating, entrapping) the active agent. Typically, the average diameter of the microspheres of the invention, which is understood as weight-average diameter as determined by laser diffraction, ranges from approximately 10 µm to approximately 500 µm. More preferably, the average microsphere diameter is between about 10 µm and about 20 µm.

The term "nanocapsules" as used herein denotes nano- or subnano-scale structures comprising an oil droplet (fine oil drops) coated with a polymeric coating forming. The polymeric coating forms a hard shell enveloping the oil core. The nanocapsules have an average diameter of between about 100 nm and about 1000 nm, preferably between about 100 nm to 900 and more preferably between about 100-300 nm to about 300-500 nm. Further, the nanocapsules' size in a microsphere is essentially uniform with about 99% of the oil droplets having a diameter below 1 micron. As used herein the term "nanocapsules" should be understood as a synonym to any polymeric coated oil droplets or oil droplets having a polymeric coating.

The term "plurality of nanocapsules" as used herein denotes two or more of such nanocapsules accommodated in the gel-forming polymer.

The active agent is enclosed within the nanocapsule. As a result, there is no direct contact between the active agent and the gel forming polymer forming the microspheres. In fact, upon wetting and swelling, the microspheres release in the GI tract the nanocapsule per se and not the "naked" active agent, that is to say, a particulate form of the active agent (e.g. drug) itself or the agent at its molecular level.

As used herein, the term "non-hydrophilic active agent" denotes any compound that is regarded as, at least to some extent, water repelling. In other words, any agent exhibiting low, medium or highly hydrophobicity or lipophilicity would be regarded as a non-hydrophilic agent. A non-hydrophilic agent may be defined by parameters characterizing the partition/distribution coefficient of the agent (as a solute) between two phases for example, an organic solvent and water (the most commonly used system being octanol-water). Typically, a partition coefficient (log P) describes the hydrophobicity of neutral compounds, while the distribution coefficient (log D, being a combination of pKa and log P) is a measure of the pH dependent hydrophobicity of the agent. A non-hydrophilic active agent in accordance with the invention is any compound having a log P>1.5.

The oil core of the nanocapsules may comprise a single oil type or a combination of oils and can be selected from a wide range of usually usable oils from polar oils to non-polar oils, as long as they do not mix with the water phase and are a liquid as a whole. According to one embodiment, the oil droplets comprise an oil selected from long chain vegetable oils, ester oils, higher liquid alcohols, higher liquid fatty acids, natural fats and oils and silicone oils. According to a preferred embodiment, the oil core comprise a natural oil such as corn oil, peanut oil, coconut oil, castor oil, sesame oil, soybean oil, perilla oil, sunflower oil, argan oil and walnut oil.

The oil droplets are each enclosed within a polymeric coating to form nanocapsules comprising the oil core and a polymeric shell surrounding the oil core. The polymeric coating provides a shell structure surrounding the oil core. The term "shell" in the context of the present invention denotes any solid or semi solid polymeric structure enclosing an oil droplet. The shell may comprise a single polymer or a combination or blend of two or more polymers as will be further discussed below. When the polymeric coating comprises a blend of polymers, it is preferable that at least one of the polymers is soluble at a pH above 5.0, or that at least one of the polymers is water soluble (pH independent).

In accordance with one embodiment, the combination of at least two polymers comprises a blend of polymers comprising a first polymer or polymers (group of polymers) which is either water soluble (pH independent) or soluble at a pH of above 5.0 and a second polymer or polymers (second group of polymers) which is water insoluble polymer.

The term "water soluble polymer" denotes any polymer which, when introduced into an aqueous phase at 25° C., at a mass concentration equal to 1%, make it possible to obtain a macroscopically homogeneous and transparent solution, i.e. a solution that has a minimum light transmittance value, at a wavelength equal to 500 nm, through a sample 0.1 cm thick, of at least 80% and preferably of at least 90%.

The term "polymer soluble at a pH above 5.0" denotes any polymer that at a pH below 5.0 and at 25° C., it does not lose more than 10% of its dry weight into the medium by dissolution, while at the same temperature, in an aqueous medium having a pH above 5.0, it forms a hydrogel or dissolved to form a macroscopically homogeneous and transparent solution. Such polymers are referred to, at times; by the term "enteric polymers".

Many water soluble polymers are known in the art. Suitable polymers in the context of the present invention comprise include, but are not limited to, polyols and polycarbohydrates. Exemplary water soluble polymers include hydroxylated celluloses, such as, for example, hydroxypropylmethyl cellulose and hydroxymethyl cellulose. Other suitable water soluble polymers include polyethylene glycol. Combinations of two or more water soluble polymers are also contemplated.

Also, many polymers which are soluble only at a pH above 5.0 are known in the art. Non-limiting examples of enteric polymers applicable with respect to the invention include, from: hydroxypropylmethylcellulose phthalate (HP55), cellulose acetate phthalate, carboxy-methylcellulose phthalate, and any other cellulose phthalate derivative, shellac, EUDRAGIT L100-55 (Poly(methacylic acid-co-ethyl acrylate)) 1:1), zein.

A preferred enteric polymer is EUDRAGIT L100-55 (Poly (methacylic acid-co-ethyl acrylate)) 1:1).

The term "water insoluble polymer" denotes any polymer which does not lose more than 10% of its dry weight into an aqueous medium by dissolution, irrespective of the pH of the medium Non-limiting examples of water insoluble polymers include cellulose esters such as di- and triacylates including mixed esters such as, for example, cellulose acetate, cellulose diacetate, cellulose triacetate, cellulose propionate, cellulose acetate butyrate, cellulose acetate propionate, cellulose tripropionate; cellulose ethers such as ethyl cellulose; nylons; polycarbonates; poly(dialkylsiloxanes); poly(methacrylic acid) esters; poly(acrylic acid) esters; poly(phenylene oxides); poly(vinyl alcohols); aromatic nitrogen-containing polymers; polymeric epoxides; regenerated cellulose; membrane-forming materials suitable for use in reverse osmosis or dialysis application; agar acetate; amylose triacetate; beta glucan acetate; acetaldehyde dimethyl acetate; cellulose acetate methyl carbamate; cellulose acetate succinate; cellulose acetate dimethylamino acetate; cellulose acetate ethyl carbonate; cellulose acetate chloroacetate; cellulose acetate ethyl oxalate; cellulose acetate propionate; poly(vinylmethylether) copolymers; cellulose acetate butyl sulfonate; cellulose acetate octate; cellulose acetate laurate; cellulose acetate p-toluene sulfonate; triacetate of locust gum bean; hydroxylated ethylene-vinyl acetate; cellulose acetate butyrate; wax or wax-like substances; fatty alcohols; hydrogenated vegetable oils; polyesters, homo and copolymer, such as polylactic acid or PLAGA and the like, and combinations thereof.

Preferred water insoluble polymers in accordance with the invention are Eudrgit RS or EUDRAGIT RL (Poly(ethyl acrylate-co-methyl methacrylate-co-trimethylammonioethyl methacrylate chloride) 1:2:0.2) or a combination of same.

When the nanocapsules comprise at least two polymers, the first polymer is water insoluble polymer and the second polymer is soluble at a pH above about 5.0.

In accordance with a preferred embodiment, the weight/weight ratio between the first polymer(s), i.e. the water insoluble polymer or group of polymers and the second group polymer(s), i.e. the polymer(s) soluble at pH above about 5.0 or group of such polymers is preferably in the range between 5:95 and 50:50.

Without being bound by theory, it is believed that the ratio between the water insoluble polymer and the polymer soluble at pH above about 5.0 (the "non-insoluble" polymer) is critical for controlling release of the active agent from the nanocapsules. Having a first polymer that is water insoluble and a second polymer that is soluble in water or soluble in water at a pH above 5.0 allows, following exposure of the nanocapsules to water or to an aqueous medium having pH above 5.0, the slow dissolution of the polymer, while the general arrangement of the insoluble polymer is essentially retained. In other words, the slow dissolution of the "non-insoluble" polymer results in the formation of channel-like pathways in a polymer "skeleton" formed from the water insoluble polymer, through which the active agent may escape the nanocapsule. In order to facilitate the control release of the active agent from the nanocapsules, it has been envisaged that a preferred ratio between the first polymer, i.e. water insoluble polymer, and the so-called "non-insoluble" polymer is that in favor of the polymer soluble at a pH above about 5.0 (e.g. a weight:weight ratio of 75:25 in favor of the water non-insoluble polymer).

According to one embodiment, the polymeric combination comprises a mixture of a first polymer or group of polymers (the insoluble polymer) selected from EUDRAGIT RL (Poly (ethyl acrylate-co-methyl methacrylate-co-trimethylammonioethyl methacrylate chloride) 1:2:0.2) or EUDRAGIT RS Poly(ethyl acrylate-co-methyl methacrylate-co-trimethylammonioethyl methacrylate chloride) 1:2:0.1) or a combination of same, and a second polymer or group of polymers (the water soluble or polymer soluble at a pH above 5.0) selected from EUDRAGIT L100-55 (Poly(methacylic acid-co-ethyl acrylate)) 1:1) and hydroxypropyl methylcellulose phthalate (HPMPC) or a combination of same. A specific selection of polymers combination in accordance with the invention comprises EUDRAGIT RS Poly(ethyl acrylate-co-methyl methacrylate-co-trimethylammonioethyl methacrylate chloride) 1:2:0.1) and EUDRAGIT L100-55 (Poly(methacylic acid-co-ethyl acrylate)) 1:1) at a weight/weight ratio of from about 25:75 to about 50:50.

The plurality nanocapsules are accommodated within a gel-forming polymer.

As used herein the term "gel forming polymer" denotes any hydrophilic polymer which when wetted, forms a network of polymers that swell up or gels. Gel forming polymers are also referred to, at times, as hydrogel forming polymers. The gel forming polymer may be a natural protein or a synthetic polymer. In accordance with one preferred embodiment of the invention, the gel forming polymer are those which when wetted, become "sticky", i.e. are capable of enhancing adhesion of the wetted microspheres and nanocapsules contained therein to the intestinal epithelium.

As used herein the term "accommodated" denotes enclosing, coating, embedding, surrounding, confining, entrapping or any other manner of incorporating the nanocapsules by the gel forming polymer(s) so as to provide a packed arrangement of a plurality of nanocapsules comprising the active agent with a second tier of protection.

Non-limiting examples of natural gel-forming polymers include, proteins, such as gelatin or collagen, and polysaccharides such as agar, carrageenan, glucomannan, scleroglucan, schizophyllan, gellan gum, alginic acid, curdlan, pectin, hyaluronic acid, or guar gum.

Non-limiting examples of synthetic gel-forming polymers include, polyacrylic acid, modified cellulose, methylcellulose, methylpropylcellulose, carboxymethyl cellulose, cationized cellulose; hydroxypropylmethylcellulose, hydroxyethylcellulose, carboxyvinyl polymer, polyvinylpyrrolidone, polyvinylacetaldiethylamino acetate, polyvinyl alcohol, sodium carboxymethycellulose, 2-methyl-5-vinylpyridine, carbomers and the like.

One aspect of the invention concerns the use of the microspheres as a delivery system of the active agent through the GI tract, i.e. for oral administration. A preferred embodiment in accordance with this aspect of the invention concerns the delivery of active agents which are substrates of the P-gp efflux pump.

Alternatively, the microspheres may be designed for administration by injection.

The term "substrate of the P-gp efflux pump" which may be used interchangeably with the term "P-gp substrate" as used herein denotes any active substance (for therapeutic, cosmetic or diagnostic purposes) that is subject to active transport, "efflux" out of cells via the P-gp membrane bound transporter. The P-gp is expressed along the entire length of the gut and also in the liver, kidney, blood brain barrier and placenta. In this context, the present invention concerns medicinal substances subjected to active transport by the intestinal p-gp which is located on the apical membranes of the epithelial cells. Utilizing the energy that is generated by hydrolysis of ATP, P-gp drives the efflux of various substrates against a concentration gradient and thus reduce their intracellular concentration and in the case of active substances, their oral bioavailability.

Thus, in accordance with one preferred embodiment of the present invention, the active agent is any medicinal, cosmetic or diagnostic substance that, following oral administration, its blood bioavailability is decreased or inhibited as a result the P-gp efflux mechanism. P-gp substrates may be categorized according to their solubility and level of metabolism. A non-limiting list of P-gp substrates according to this classification includes:

High solubility and extensive metabolism: amitryptyline, cochicine, dexamethasone, diltiazem, ethinyl estradiol;

Low solubility and extensive metabolism: atorvastatin, azithromycin, carbamazepine, cyclosporine, glyburide, haloperidol, itraconazole, tacrolimus sirolimus, ritonavir. sanquinavir, lovastatin.

High solubility and poor metabolism: amiloide, amoxicillin, chloroquine, ciprofloxacin, dicloxacillin, erythromycin, fexofenadine, levodopa, midazolam, morphine, nifedipine, primaquine, promazine, promethazine, quinidine, quinine; and Low solubility and poor metabolism—ciprofloxacin and talinolol.

In the context of the present invention, the non-hydrophilic active agent is a lipophilic or amphipathic compounds or complexes or mixtures containing such compounds. The non-hydrophilic active agent also includes hydrophilic compounds which have been modified, e.g. by the attachment of a lipophilic moiety, to increase the lipophilicity of the agent. These modified compounds are referred to herein, at times, by the term "prodrug".

The active agent may be in free acid, free base or salt form, and mixtures of active agents may be used.

In accordance with one embodiment, the active agent is a lipophilic agent. The term "lipophilic agent" is used herein to denote any compound that has a log P (octanol/water)>2.0-3.0 and a triglyceride (TG) solubility, as measured, for example, by solubility in soybean oil or similar, in excess of 10 mg/mL. This definition includes medium lipophilic drugs i.e. having a log P between 3.0 to 6, as well as highly lipophilic drugs, having a log P>6.

Examples of medium to lipophilic therapeutically active agents which may be suitable for entrapment in the nanocapsules according to the present invention include the following:

Analgesics and anti-inflammatory agents: aloxiprin, auranofin, azapropazone, benorylate, diflunisal, etodolac, fenbufen, fenoprofen calcim, flurbiprofen, ibuprofen, indomethacin, ketoprofen, meclofenamic acid, mefenamic acid, nabumetone, naproxen, oxyphenbutazone, phenylbutazone, piroxicam, sulindac.

Anthelmintics: albendazole, bephenium hydroxynaphthoate, cambendazole, dichlorophen, ivermectin, mebendazole, oxamniquine, oxfendazole, oxantel embonate, praziquantel, pyrantel embonate, thiabendazole.

Anti-arrhythmic agents: amiodarone, disopyramide, flecamide acetate, quinidine sulphate.

Anti-bacterial agents: benethamine penicillin, cinoxacin, ciprofloxacin, clarithromycin, clofazimine, cloxacillin, demeclocycline, doxycycline, erythromycin, ethionamide, imipenem, nalidixic acid, nitrofurantoin, rifampicin, spiramycin, sulphabenzamide, sulphadoxine, sulphamerazine, sulphacetamide, sulphadiazine, sulphafurazole, sulphamethoxazole, sulphapyridine, tetracycline, trimethoprim.

Anti-coagulants: dicoumarol, dipyridamole, nicoumalone, phenindione.

Anti-depressants: amoxapine, maprotiline, mianserin, nortriptyline, trazodone, trimipramine maleate.

Anti-diabetics: acetohexamide, chlorpropamide, glibenclamide, gliclazide, glipizide, tolazamide, tolbutamide.

Anti-epileptics: beclamide, carbamazepine, clonazepam, ethotoin, methoin, methsuximide, methylphenobarbitone, oxcarbazepine, paramethadione, phenacemide, phenobarbitone, phenyloin, phensuximide, primidone, sulthiame, valproic acid.

Anti-fungal agents: amphotericin, butoconazole nitrate, clotrimazole, econazole nitrate, fluconazole, flucytosine, griseofulvin, itraconazole, ketoconazole, miconazole, natamycin, nystatin, sulconazole nitrate, terbinafine, terconazole, tioconazole, undecenoic acid.

Anti-gout agents: allopurinol, probenecid, sulphin-pyrazone.

Anti-hypertensive agents: amlodipine, benidipine, darodipine, dilitazem, diazoxide, felodipine, guanabenz acetate, isradipine, minoxidil, nicardipine, nifedipine, nimodipine, phenoxybenzamine, prazosin, reserpine, terazosin.

Anti-malarials: amodiaquine, chloroquine, chlorproguanil, halofantrine, mefloquine, proguanil, pyrimethamine, quinine sulphate.

Anti-migraine agents: dihydroergotamine mesylate, ergotamine tartrate, methysergide maleate, pizotifen maleate, sumatriptan succinate.

Anti-muscarinic agents: atropine, benzhexyl, biperiden, ethopropazine, hyoscyamine, mepenzolate bromide, oxyphencylcimine, tropicamide.

Anti-neoplastic agents and Immunosuppressants: aminoglutethimide, amsacrine, azathioprine, busulphan, chlorambucil, cyclosporin, dacarbazine, estramustine, etoposide, lomustine, melphalan, mercaptopurine, methotrexate, mitomycin, mitotane, mitozantrone, procarbazine, tamoxifen citrate, testolactone. tacrolimus, sirolimus Anti-protozoal agents: benznidazole, clioquinol, decoquinate, diiodohydroxyquinoline, diloxanide furoate, dinitolmide, furzolidone, metronidazole, nimorazole, nitrofurazone, ornidazole, timidazole.

Anti-thyroid agents: carbimazole, propylthiouracil.

Alixiolytic, sedatives, hypnotics and neuroleptics: alprazolam, amylobarbitone, barbitone, bentazepam, bromazepam, bromperidol, brotizolam, butobarbitone, carbromal, chlordiazepoxide, chlormethiazole, chlorpromazine, clobazam, clotiazepam, clozapine, diazepam, droperidol, ethinamate, flunanisone, flunitrazepam, fluopromazine, flupenthixol decanoate, fluphenazine decanoate, flurazepam, baloperidol, lorazepam, lormetazepam, medazepam, meprobamate, methaqualone, midazolam, nitrazepam, oxazepam, pentobarbitone, perphenazine pimozide, prochlorperazine, sulpiride, temazepam, thioridazine, triazolam, zopiclone.

beta-Blockers: acebutolol, alprenolol, atenolol, labetalol, metoprolol, nadolol, oxprenolol, pindolol, propranolol.

Cardiac Inotropic agents: amrinone, digitoxin, digoxin, enoximone, lanatoside C, medigoxin.

Corticosteroids: beclomethasone, betamethasone, budesonide, cortisone acetate, desoxymethasone, dexamethasone, fludrocortisone acetate, flunisolide, flucortolone, fluticasone propionate, hydrocortisone, methylprednisolone, prednisolone, prednisone, triamcinolone.

Diuretics: acetazolamide, amiloride, bendrofluazide, bumetanide, chlorothiazide, chlorthalidone, ethacrynic acid, frusemide, metolazone, spironolactone, triamterene.

Anti-parkinsonian agents: bromocriptine mesylate, lysuride maleate.

Gastro-intestinal agents: bisacodyl, cimetidine, cisapride, diphenoxylate, domperidone, famotidine, loperamide, mesalazine, nizatidine, omeprazole, ondansetron, ranitidine, sulphasalazine.

Histamine H-Receptor Antagonists: acrivastine, astemizole, cinnarizine, cyclizine, cyproheptadine, dimenhydrinate, flunarizine, loratadine, meclozine, oxatomide, terfenadine.

Lipid regulating agents: bezafibrate, clofibrate, fenofibrate, gemfibrozil, probucol.

Nitrates and other anti-anginal agents: amyl nitrate, glyceryl trinitrate, isosorbide dinitrate, isosorbide mononitrate, pentaerythritol tetranitrate.

Nutritional agents: betacarotene, vitamin A, vitamin $B_2$, vitamin D, vitamin E, vitamin K.

HIV protease inhibitors: Nelfinavir,

Opioid analgesics: codeine, dextropropyoxyphene, diamorphine, dihydrocodeine, meptazinol, methadone, morphine, nalbuphine, pentazocine.

Sex hormones: clomiphene citrate, danazol, ethinyl estradiol, medroxyprogesterone acetate, mestranol, methyltestosterone, norethisterone, norgestrel, estradiol, conjugated oestrogens, progesterone, stanozolol, stibestrol, testosterone, tibolone.

Stimulants: amphetamine, dexamphetamine, dexfenfluramine, fenfluramine, mazindol.

Without being limited thereto, preferred drugs in accordance with the invention include tacrolimus, sirolimus halofantrine, ritonavir. loprinavir, amprenavir, saquinavir, calcitrol, dronabinol, isotretinoin, tretinoin, risperidone base, valproic acid while preferred pro-drugs include dexamethasone palmitate, paclitaxel palmitate, docetaxel palmitate.

Some non-limiting examples of lipophilic drugs which may be incorporated in the delivery system of the present invention and their medical applications are described by Robert G. Strickley [Strickley R. G. Pharmaceutical Research, 21(2):201-230; (2004)] and by Kopparam Manjunath, et al. [Manjunath K. et al., Journal of Controlled Release 107:215-228; (2005)].

In accordance with another embodiment, the active agent is an amphipathic agent. The term "amphipathic agent" is used herein to denote any compound that has a log P value between 1.5-2.5 and a triglyceride (TG) solubility, as measured, for example, by solubility in soybean oil or similar, in excess of 10 mg/mL.

Examples of amphipathic active agents which may be delivered by the system of the invention include, without being limited thereto, pysostigmine salicylate, chlorpromazine, fluphenazine, trifluoperazine, and lidocaine, bupivacaine, amphotericin B, etoposide, teniposide and antifungal echinocandins and azoles, such as clotrimazole and itaconazole.

Another example of a therapeutically, non-hydrophilic active agent suitable for entrapment in the nanocapsules according to the invention include, without being limited thereto is clozapine. Clozapine is an effective atypical antipsychotic drug applied in the treatment of resistant schizophrenia. Clozapine is rapidly absorbed orally with a bioavailability of 27%. Clozapine is extensively metabolized by hepatic microsomal enzymes (CYP1A2 and CYP3A4) and forms N-demethyl and N-oxide metabolites Thus, clozapine is a good candidate for delivery by the system of the present invention.

The invention also provides a method of preparing the microspheres accommodating a plurality of nanocapsules in accordance with the present invention, the method comprises:
  (a) providing an organic phase comprising oil, a water miscible organic solvent, a non-hydrophilic active agent dissolved in the solvent and a polymer or combinations of polymers for coating the oil core;
  (b) slowly adding water to said organic phase to obtain a water in oil emulsion;
  (c) continuously adding, preferably drop wise, water to the water in oil emulsion to induce phase inversion of the emulsion thereby obtaining oil in water (o/w) emulsion;
  (d) mixing the o/w emulsion with a gel forming polymer or a combination of gel forming polymers;
  (e) removing the organic solvent and water to obtain microspheres accommodating a plurality of nanocapsules. It is essential to note that the nanocapsules comprise an oil core in which the active agent is dissolved or dispersed and that this oil core is enclosed by a polymeric shell. The plurality of shell coated oil cores are accommodated in the gel forming polymer, such that there is no direct contact between the agent and the gel forming polymer.

The organic solvent used in the method of the invention may be any organic solvent miscible with water that has a boiling point close or lower than the boiling point of water. A non-limiting list of such organic solvents includes ethanol, methanol, acetone, ethyl acetate, isopropanol (bp 108° C., nonetheless regarded as volatile in the context of the present invention).

The use of a combination of oil and organic solvent enables the encapsulation within the nanocapsules of various agents which are essentially non-hydrophilic in nature. The oil core may also include one or more non-hydrophilic excipients (e.g. lipophilic excipients). To this end, the method of the invention may also include the addition of the one or more excipients in the organic phase. The excipient is preferably any excipient having at least 1% solubility in an oil phase. According to one example, the excipient is a lipophilic surfactant, such as labrafil M 1944 CS, polysorbate 80, polysorbate 20.

To the oil containing organic phase, water is slowly added, essentially, drop-wise. At beginning, oil in water emulsion is formed, i.e. drops of water are dispersed in the organic phase. However, continuous slow addition of water to the medium eventually results in an inverse phenomenon, where the continuous and non-continuous are 'switched' such that oil droplets coated with the polymer coating are dispersed in water.

The term "emulsion" used herein to denote a system having at least two liquid phases, one of which is dispersed in the other. The dispersed phase is also referred to as inner phase, discontinuous phase, incoherent phase (the dispersed droplets) while the outer phase may also be referred to as coherent or continuous phase. Emulsions may comprise more than two phases. For example, they may be comprised of three liquid phases (i.e. triple emulsions), or two liquid phases and a solid phase. Common to all emulsions is that their outer phase is in a liquid state. If a third phase is present, such as a liquid or solid phase, this is usually dispersed in the dispersed phase which is dispersed in the outer phase. An emulsifying agent may or may not also be present.

The different types of emulsions may be defined by reference to the type of liquid forming the outer phase vs. the type of liquid forming the dispersed phase. In this connection, when an oil phase is dispersed in a water phase, the emulsion is terms "oil in water emulsion" or the "normal emulsion". However, it is also possible to form an "inverse or water in oil (w/o) emulsion". In an inverse emulsion, the water droplets are dispersed in a continuous phase of oil.

When forming nanocapsules, initially water in oil emulsion is formed and this w/o emulsion is converted to an o/w emulsion by the addition of water to the oil/organic phase. Without being bound by theory, it is believed that as a result, the polymers in the system deposit at the oil water interface entrapping all the internal oil droplets and isolating them from the continuous aqueous phase. The resulting emulsion comprising the oil droplets coated with the coating polymer(s) is then mixed with the solution of the gel forming polymer. Once the oil in water emulsion is formed and the gel forming polymer is added, the solvent (or mixture of solvents) and the water are essentially removed.

There are several techniques available for removing a solvent (or solvent combination) from an emulsion, as known to those versed in the art including heating and solvent evaporation, volatile solvent evaporation followed by lyophilization etc. According to the invention, the solvent is preferably removed by spray drying, provided the active agents are not heat sensitive. In case the active agents are heat sensitive, other methods for removing solvent from an emulsion may be used, as known and appreciated by those versed in the art.

Spray drying is a mechanical microencapsulation method developed in the 1930s. Accordingly, the emulsion is atomized into a spray of droplets by pumping the slurry through a rotating disc into the heated compartment of a spray drier. There, the solvent as well as the water in the emulsion, are evaporated to obtain the dry microspheres.

The resulting dry microspheres may be formulated in accordance with any desired application. There are almost limitless applications for such microencapsulated material. Depending inter alia, on the active agent, the microspheres may be applicable in agriculture, pharmaceuticals, foods, cosmetics and fragrances, textiles, paper, paints, coatings and adhesives, printing applications, and many other industries.

In accordance with a preferred embodiment, the microspheres are for use in medicine, cosmetics or diagnosis.

More preferably, the dry microspheres are formulated as a pharmaceutical composition, preferably for oral administration. To this end, the dry microspheres may be included in an enteric vehicle, such as an enteric capsule. Non-limiting examples of enteric capsules include soft or hard enterocoated capsules as known in the art.

It is noted that when the dry microspheres are protected from gastric fluids by the use of such an enteric vehicle, the oil droplets (in the nanocapsules) do not need to be coated with a polymer that is soluble at a pH above 5.0. In other words, a combination of a water soluble polymer and a water insoluble polymer is applicable.

On the other hand, using a blend of polymers comprising a polymer which is soluble only at a pH above 5.0, other delivery forms of the microspheres are possible, such as in the form of sachets.

Thus, it is understood that depending on the specific type of formulation, a pharmacists or any other formulator can determine the specific combination of polymers to be use in accordance with the invention.

For oral delivery tablets, pills, powders, lozenges, sachets, cachets, elixirs, suspensions, aerosols (as a solid or in a liquid medium), and sterile packaged powders as well as other delivery forms may be used.

The microspheres of the invention were shown to provide elevated blood levels of the active agents exemplified as compared to commercial products or to an emulsion formulation (denominated oil in the results section).

According to one embodiment, the microcapsules of the invention provide controlled release of the active agent. As used herein, "controlled release" means any type of release which is not immediate release. For example, controlled release can be designed as modified, extended, sustained, delayed, prolonged, or constant (i.e. zero-order) release. In theory, one of the most useful release profiles is constant release over a predetermined period of time. It is contemplated that the controlled release of the agent is obtained by the coating applied to the droplets and that the release profile of the active agent may be dictated by variations in the composition of the polymers forming the shell. The rate-controlling polymer coat may also be built up by applying a plurality of coats of polymer blends on to the core droplet as known in the art.

It is noted that by the method of the invention the microspheres are constructed such that there is no direct contact between the active agent and the gel-forming polymer (which can be a blend of the gel-forming polymers). Further, it is noted that the method of the invention allows any excess of the shell forming polymers to blend with the gel forming polymer, i.e. form part of the microsphere coating over the nanocapsules. Thus, upon contact of the final product with an aqueous environment, the gel forming polymer jellifies and swells while the excess of water soluble polymer(s) or polymer(s) soluble at a pH above 5.0 which have been blended with the gel forming polymer are dissolved. Without being bound by theory, it is believed that by this combination of the gel forming polymer and the excess of other polymer (used in the construction of the nanocapsule's wall) in the microsphere structure, intact nanocapsules comprising the active agent are released from the microsphere (assumably through gaps formed in the microsphere as a result of the dissolution of the soluble polymers) and not the drug in its free form. It is believed, again, without being bound by theory, that the release of nanocapsules from the gel and not the drug in its free form, permits the escape of the agent from the P-gp efflux and thereby their uptake by the lymph vessels.

The invention also provides a method of increasing bioavailability of an active agent in a human subject's body, the method comprises providing said subject with the microspheres of the invention. The results presented herein show that by the use of the microspheres in accordance with the invention bioavailability of the tested active agents in the blood may increase, at least by a factor of 1.3, preferably by a factor of 2, more preferably by a factor of 3, with respect to control drugs used (see for example FIG. 12).

The invention also provides a method of treating a subject for a pathological condition which requires for said treatment an effective amount of an active agent within the subject's blood system, the method comprises providing said subject with the microspheres of the invention.

The term "pathological condition" used herein denotes any condition which requires for improving the well-being of the subject the delivery, of an active agent being a drug or prodrug or diagnostic agent, such as those listed hereinabove. When the active agent is a non-hydrophilic entity, such as, without being limited thereof, a lipophilic agent or an amphipathic agent, or any lipophilic/amphipathic derivative of an active agent, the delivery of the active agent in accordance with the invention is preferably, via lymphatic transport. The non-limiting list of conditions includes, inter alia, inflammation and autoimmune disorders, parasitism (e.g. malaria) bacterial, viral or fungal infection, cardiac disorders (e.g. arrhythmia), coagulation disorders, depression, diabetics, epilepsy, migraine, cancer, immune disorders, hormonal disorders, psychiatric conditions, gastrointestinal tract disorders, nutritional disorders, and many others, as known in the art.

The effective amount of active agent in the pharmaceutical composition and unit dosage form thereof may be varied or adjusted widely depending upon the particular application, the manner or introduction, the potency of the particular active agent, the loading of the agent into the nanocapsule, and the desired concentration. The effective amount is typically determined in appropriately designed clinical trials (dose range studies) and the person versed in the art will know how to properly conduct such trials in order to determine the effective amount. As generally known, an effective amount depends on a variety of factors including the hydrophibiclity of the active agent and when relevant, the lipophilicity/amphipathicy, the selection of polymers forming the nanocapsule (the oil droplet's coating) and/or the outer gel forming envelop, the distribution profile of the active agent within the body after being released from the nanocapsule, a variety of pharmacological parameters such as half life in the body, on undesired side effects, if any, on factors such as age and gender, etc.

The term "unit dosage forms" refers to physically discrete units suitable as unitary dosages for human subjects and other mammals, each unit containing a predetermined quantity of the active agent calculated to produce the desired therapeutic effect, in association with suitable pharmaceutical excipients. The concentration of therapeutically active agent may vary.

The composition of the invention may be administered over an extended period of time in a single daily dose, in several doses a day, as a single dose and in several days, etc. The treatment period will generally have a length proportional to the length of the disease process and the specific microsphere's effectiveness (e.g. effective delivery via the lymphatic system, effectiveness of the agent etc.) and the patient species being treated.

As appreciated, while the invention is described in the following detailed description with reference to the microspheres and methods for their preparation, it is to be understood that also encompassed within the present invention are pharmaceutical compositions comprising them and therapeutic methods making use of same, as well as any other use of the microspheres.

As used in the specification and claims, the forms "a", "an" and "the" include singular as well as plural references unless the context clearly dictates otherwise. For example, the term "a polymer" includes one or more polymers and the term "oil" includes one or more oils.

Further, as used herein, the term "comprising" is intended to mean that the microspheres include the recited elements, but not excluding others. The term "consisting essentially of" is used to define microspheres that include the recited elements but exclude other elements that may have an essential significance on the bioavailability of the lipophilic agent within a subject's body. For example, microspheres consisting essentially of oil droplets coated by a water soluble polymer (pH independent) will not include or include only insignificant amounts (amounts that will have an insignificant effect on the release of the non-hydrophilic agent from the microsphere) of polymers that are pH dependent with respect to their solubility, such as enteric polymers. "Consisting of" shall thus mean excluding more than trace elements of other elements. Embodiments defined by each of these transition terms are within the scope of this invention.

Further, all numerical values, e.g. when referring the amounts or ranges of the elements constituting the microspheres, are approximations which are varied (+) or (−) by up to 20%, at times by up to 10% of from the stated values. It is to be understood, even if not always explicitly stated that all numerical designations are preceded by the term "about".

DESCRIPTION OF SOME NON-LIMITING EMBODIMENTS

Example 1

Nanocapsules Accommodated in Microshperes

Materials and Methods
Materials

Poly(ethyl arylate, methyl methacrylate, trimethylammonioethyl methacrylate chloride) 1:2:0.2 (EURDRAGIT RL), Poly(ethyl acrylate, methyl methacrylate, trimethylammonioethyl methacrylate chloride) 1:2:0.1 (EURDRAGIT RS PO) and Poly(methacrylic acid, Ethyl acrylate) 1:1 (EUDRAGIT L100-55 (Poly(methacylic acid-co-ethyl acrylate)) 1:1)) were purchased from Rohm (Dramstadt, GmbH, Germany), Hydroxypropyl methylcellulose phthalate (HP-MCP 55 NF) was obtained from Eastman (Rochester, USA). Hydroxypropyl methylcellulose (Methocel E4M Premium) was obtained from Dow Chemical Company (Midland, Mich., USA), Methylcellulose (Metolose 90SH 100,000) was obtained from Shin-Etsu (Tokyo, Japan), Argan Oil was purchased from Alban-Muller (Vincenny, France), Polyoxyethylated oleic glycerides (Labrafil M 1944 CS) was kindly donated by Gattefosse (St. Priest, France), Dexamethasone palm itate (DXPL) was synthesized as described in 2.1, tacrolimus (as monohydrate) was purchased from Concord Biotech Limited (Ahmedabad, India), Amphotericin B may be purchased from Alpharma (Lot N:A1960561). Other chemicals and solvents were of analytical reagent grade and double-distilled water was used throughout the study.

Methods
Preparation of the Nanocapsules

Various preliminary formulations were prepared as described in Tables 1 and 2.

Two different solvent addition approaches were used in the present study for nanocapsule preparation. The first approach is based on the well-established method of Fessi et al. [Fessi H, et al. Nanocapsule formation by interfacial polymer deposition following solvent displacement. Int J Pharm 1989 55:R1-R4 (1989).] using the interfacial deposition of a coating polymer following displacement of a semi-polar co-solvent system (acetone:ethanol; 19:1) miscible with water from an oil/organic phase. The acetone solution comprising the oil phase, the lipophilic surfactant, the coating polymers (nanocapsule envelope forming polymers) and the respective drug is poured into an aqueous solution comprising eventually an emulsion stabilizer. The aqueous phase immediately turns milky with bluish opalescence as a result of the nanocapsule formation (Table 1). Whereas, in the nanocapsule formulations presented in Table 2, the water phase is added slowly to the acetone:ethanol/organic phase leading first to the formation of a w/o microemulsion which upon continuous water addition yields an inverse o/w emulsion resulting in the formation of nanocapsules following displacement of the dipolar solvents.

TABLE 1

Composition of nanocapsule formulations prepared by interfacial acetone displacement diffusion according to the method of Fessi et al (24 = 26)

| | Organic Phase composition | | | | | | Aqueous phase | | |
| --- | --- | --- | --- | --- | --- | --- | --- | --- | --- |
| No. | Acetone:Ethanol (19:1), ml | Oil* ml | 1st Polymer, g | | 2nd Polymer, g | | Water ml | Methocel E4M, g | Comments |
| 1 | 40 | 1 | Eud. RL | 0.90 | HPMCP | 0.10 | 150 | 1 | |
| 2 | 40 | 1 | Eud. RL | 0.90 | HPMCP | 0.10 | 150 | 1 | |
| 3 | 40 | 1 | Eud. RL | 0.90 | HPMCP | 0.10 | 150 | 0 | With fluorescent |
| 4 | 40 | 1 | Eud. RL | 0.90 | HPMCP | 0.10 | 150 | 0 | With fluorescent |
| 5 | 40 | 1 | Eud. RL | 0.90 | — | — | 150 | 1 | |
| 6 | 40 | 1 | Eud. RL | 0.95 | HPMCP | 0.05 | 150 | 1 | |
| 7 | 100 | 0.6 | Eud. RL | 0.95 | HPMCP | 0.05 | 250 | 1 | |
| 8 | — | 0.6 | Eud. RL | 0.95 | HPMCP | 0.05 | 250 | 1 | 100 ml Ethanol |
| 9 | 50 | 0.6 | Eud. RL | 0.95 | HPMCP | 0.05 | 250 | 1 | |
| 10 | 50 | 0.6 | Eud. RL | 0.90 | Eud. | 0.10 | 250 | 1 | |
| 11 | 100 | 0.6 | Eud. RL | 0.90 | Eud. | 0.10 | 250 | 1 | |
| 12 | 100 | 0.6 | Eud. RS | 0.90 | Eud. | 0.10 | 250 | 0 | |
| 13 | 100 | 0.6 | Eud. RS | 0.90 | Eud. | 0.10 | 200 | 1 | |
| 14 | 100 | 0.6 | Eud. RS | 0.90 | Eud. | 0.10 | 200 | 1 | |
| 15 | 100 | 0.6 | Eud. RS | 0.90 | Eud. | 0.10 | 200 | 0 | With Lactose |
| 16 | 100 | 0.6 | Eud. RS | 0.25 | Eud. | 0.75 | 75 | 1 | |
| 17 | 100 | 0.6 | Eud. RS | 0.50 | Eud. | 0.50 | 75 | 1 | |
| 18 | 100 | 0.6 | Eud. RS | 0.75 | Eud. | 0.25 | 75 | 1 | |

*The oil phase comprised: Argan oil:Labrafil M 1944 CS; 5:1 and DXPL at a constant concentration of 5% with respect to the argan oil volume.

TABLE 2

Composition of nanocapsule formulations prepared by polymer interfacial nanodeposition using the solvent extraction process following emulsion phase inversion (the aqueous phase is poured in the acetonic phase)

| | Aqueous phase | | Organic Phase composition | | | | | | |
| --- | --- | --- | --- | --- | --- | --- | --- | --- | --- |
| No. | Water ml | Methocel E4M gr | Acetone:Ethanol (19:1), ml | Oil* ml | 1st Polymer g | | 2nd Polymer g | | Comments |
| 19 | 75 | 1 | 100 | 0.5 | Eud. RS | 0.90 | Eud. L100-55 | 0.10 | |
| 20 | 75 | 1 | 100 | 0.5 | — | — | — | — | |
| 21 | 75 | 0 | 100 | 0.5 | — | — | — | — | With lactose |
| 22 | 75 | 0 | 100 | 0.5 | Eud. RS | 0.75 | Eud. L100-55 | 0.25 | With lactose |
| 25 | 75 | 0 | 100 | 0.5 | Eud. RS | 0.25 | Eud. L100-55 | 0.75 | With |
| 26 | 75 | 0 | 100 | 0.5 | Eud. RS | 0.25 | Eud. L100-55 | 0.75 | With Eud. |
| 27 | 75 | 0 | 100 | 0.5 | Eud. RS | 0.25 | Eud. L100-55 | 0.75 | With Eud. |
| 28 | 75 | 1 | 100 | 0.5 | Eud. RS | 0.25 | Eud. L100-55 | 0.75 | |
| 29 | 75 | 1 | 100 | 0.5 | Eud. RS | 0.25 | Eud. L100-55 | 0.75 | |
| 30 | 75 | 1 | 100 | 0.5 | Eud. RS | 0.75 | Eud. L100-55 | 0.25 | |
| 31 | 75 | 1 | 100 | 0.5 | Eud. RS | 0.25 | Eud. L100-55 | 0.75 | |

*The oil phase comprised: Argan oil:Labrafil M 1944 CS, 5:1 and DXPL at a constant concentration of 5% with respect to the argan oil volume or Tacrolimus at a constant concentration of 4% with respect to the argan oil volume.

It should be emphasized that tacrolimus is a very expensive and toxic drug which needs to be processed carefully. It was, therefore, decided to carry out preliminary experiments with a dexamethasone palmitate (DXPL), a lipophilic drug which served as a model drug particularly for the evaluation of the in vitro release kinetic experiments.

Synthesis of Dexamethasone Palmitate

Dexamethasone (1 equivalent) was dissolved in freshly dried pyridine (2.5 ml of pyridine for each 1 gram of dexamethasone). The resulting solution was diluted 1 to 5 with dichloromethane and cooled to 4° C. on an ice bath (solution A). Palmitoyl chloride (1.2 equivalent, Aldrich) was dissolved in dichloromethane (15 ml of dichloromethane for each 1 gram of palmitoyl chloride) and also cooled to 0° C. (solution B). Solution B was transferred to a pressure-equalizing funnel and added dropwise to the vigorously-stirred and cooled solution A. After addition is complete (30 min for 5 g of dexamethasone), the reaction mixture was flushed with nitrogen, capped and left to stir on the ice bath overnight. A sample was taken next morning for evaluation of the reaction progress by thin layer chromatography, eluted by ethyl acetate:hexane (3:1 by vol.). Three major peaks were usually obtained: the first represents dexamethasone, the second is palmitoyl chloride and the third represents the product dexamethasone palmitate. In case of incompletion of the reaction, the mixture is left to stir for an additional 12 hours. At the end of this period, the organic solvent is removed under reduced pressure (not heated over 60° C.). To the residue are added 100 ml of a 2:1 ethyl acetate:hexane mixture. The resulting suspension is stirred vigorously and filtered through Buckner funnel. The semisolid is washed with ethyl acetate and the resulting filtrate is separated. The organic layer is washed twice with 100 ml of 5% cold sodium hydroxide solution, twice with water and once with sodium chloride saturated solution. The organic layer is filtered over anhydrous sodium sulfate and evaporated to dryness. The residue is dissolved in a minimal volume of chloroform and applied to a silica column (40 cm long) for flash chromatography. The column is eluted with chloroform:hexane (1:1) and dexamethasone palmitate-rich fractions are combined, evaporated to dryness and the purity of the product checked by HPLC. The yield is actually 60%

Tacrolimus Nanocapsule Preparation

EUDRAGIT RS Poly(ethyl acrylate-co-methyl methacrylate-co-trimethylammonioethyl methacrylate chloride) 1:2:0.1), EUDRAGIT L100 55 (Poly(methacylic acid-co-ethyl acrylate)) 1:1), LABRAFIL 1944 CS, argan oil and tacrolimus at the concentrations depicted in Table 3 were dissolved into 100 ml of Acetone:Ethanol (90:10) solution (oil phase). 75 ml of water was added (within 2 minutes) to the oil phase to form a dispersion. To the dispersed solution, a 200 ml of 0.5% of methylcellulose solution was added prior to the spray drying procedure. The methylcellulose and last water portion are added only after nanocapsule formation. Unless otherwise stated, methylcellulose refers to METHOCEL E4M.

Three formulations are exemplified herein: Formulations Nos. 29 and 30 which their contents are described in Tables 3, 4. These formulations differ by their polymer proportions: EUDRAGIT RS Poly(ethyl acrylate-co-methyl methacrylate-co-trimethylammonioethyl methacrylate chloride) 1:2:0.1): EUDRAGIT L100 55 (Poly(methacylic acid-co-ethyl acrylate)) 1:1) 25:75 or 75:25 respectively. A further formulation is formulation No. 32 which has similar contents as formulation No. 29, however, without EUDRAGIT RS Poly (ethyl acrylate-co-methyl methacrylate-co-trimethylammonioethyl methacrylate chloride) 1:2:0.1) and EUDRAGIT L100 55 (Poly(methacylic acid-co-ethyl acrylate)) 1:1).

TABLE 3

Composition of nanocapsule formulation No. 29

| # | Material Name | Amount | Unit |
|---|---|---|---|
| 1 | Acetone | 95 | ml |
| 2 | EURAGIT RS Poly(ethyl acrylate-co-methyl methylacrylate-co-trimethylammonioethyl methacrylate chloride) 1:2:0.1)* | 0.25 | g |
| 3 | EURAGIT L100-55 (Poly(methacyclic acid-co-ethyl)) 1:1)* | 0.75 | g |
| 4 | Ethanol | 5 | ml |
| 5 | Argan Oil | 0.5 | ml |
| 6 | Labrafil M 1944 CS | 0.1 | ml |
| 7 | Tacrolimus | 20 | mg |
| 8 | DD water | 75 | ml |
| 9 | Methocel E4M | 1 | g |
| 10 | DD water | 200 | ml |

*Formulation 32 is identical in content to formulation 29 without EURAGIT RS Poly(ethyl acrylate-co-methyl methylacrylate-co-trimethylammonioethyl methacrylate chloride) 1:2:0.1) and EURAGIT (Poly(methacyclic acid-co-ethyl)) 1:1) 110-55.

TABLE 4

Composition of nanocapsule formulation No. 30

| # | Material Name | Amount | Unit |
|---|---|---|---|
| 1 | Acetone | 95 | ml |
| 2 | EURAGIT RS Poly(ethyl acrylate-co-methyl methylacrylate-co-trimethylammonioethyl methacrylate chloride) 1:2:0.1) | 0.75 | g |
| 3 | EURAGIT L100-55 (Poly(methacyclic acid-co-ethyl)) 1:1) | 0.25 | g |
| 4 | Ethanol | 5 | ml |
| 5 | Argan Oil | 0.5 | ml |
| 6 | Labrafil M 1944 CS | 0.1 | ml |
| 7 | Tacrolimus | 20 | mg |
| 8 | DD water | 75 | ml |
| 9 | Methocel E4M | 1 | g |
| 10 | DD water | 200 | ml |

Amphotericin B Nanocapsules Preparation

EUDRAGIT RS Poly(ethyl acrylate-co-methyl methacrylate-co-trimethylammonioethyl methacrylate chloride) 1:2:0.1), EUDRAGIT L100 55 (Poly(methacylic acid-co-ethyl acrylate)) 1:1), Labrafil 1944 CS, argan oil and (Amphotericin solubilized with acetic acid) at the concentrations depicted in Table 3 were dissolved into 100 ml of Acetone:Ethanol (90:10) solution (the "organic phase"). 75 ml of water was added (within 2 minutes) to the organic phase resulting in the formation of a dispersion. To the dispersed solution, 200 ml of 0.5% hydroxypropylmethylcellulose solution was added prior to the spray drying procedure. The hydroxypropylmethylcellulose and last water portion are added only after nanocapsule formation, hydroxypropylmethylcellulose refers to Methocel E4M. The nanocapsule formulation is presented in presented in Table 5.

TABLE 5

Composition of Amphotericin A nanocapsule formulation

| No. | Material Name | Amount | |
|---|---|---|---|
| 1 | Acetone | 90 | ml |
| 2 | EURAGIT RS Poly(ethyl acrylate-co-methyl methylacrylate-co-trimethylammonioethyl methacrylate chloride) 1:2:0.1) | 0.25 | g |
| 3 | EURAGIT L100-55 (Poly(methacyclic acid-co-ethyl)) 1:1) | 0.75 | g |
| 4 | Ethanol | 10 | ml |
| 5 | Argan Oil | 1 | ml |
| 6 | Labrafil M 1944 CS | 0.2 | ml |

TABLE 5-continued

Composition of Amphotericin A nanocapsule formulation

| No. | Material Name | Amount |
| --- | --- | --- |
| 7 | Amphotericin | 60 mg |
| 8 with 1% Phosphotungstic Acid (PTA). The samples were dried and examined by TEM (Phillips CM-12; Philips, Eindhoven, The Netherlands).

Absorption Studies in Rats

The study was approved by the local ethical committee of laboratory animal care in accordance with the rules and guidelines concerning the care and use of laboratory animals MD 104.01-3. Sprague Dawley rats weighting 300-325 g were used in this study. The animals were housed in SPF conditions, and fasted 24 hours before experiment. The following morning, the animals were dosed by oral gavage, in the fasted state, with 0.2 mg/rat of tacrolimus formulated either as a suspension of Prograf® capsule content (lot—5C5129B exp.—June 2007, Fujisawa Ltd. UK) (CAPS), an oil-in-water emulsion (OIL), or as the novel DDS (formulations No. 29 and 30) or formulation 32.

Blood samples (100-150 µL) were taken from the rat tail at 0, 30 min and 1, 2, 3, 4, 6 and 24 hours from dosage administration. The blood samples were collected in heparin containing tubes. The samples were immediately frozen at −20° C. and assayed for tacrolimus levels using PRO-Trac™ II ELISA kit (DiaSorin, USA) following the protocol suggested by the company. This ELISA method is well accepted in clinical practice and is able to detect accurately tacrolimus blood levels from 0.3 to 30 ng/ml.

Bioavailability Calculations

Each rat was dosed with 160 µg/kg tacrolimus by I.V. bolus using original Prograf® concentrate for infusion ampoule 5 mg/ml (lot: 5A3098H exp: November 2006, Fujisawa Ltd. UK). Blood samples (100-150 µL) were taken from animal tail at 5, min and 1, 2, 3, 4, 6 and 24 hours. The samples were treated and analyzed as described above. The pharmacokinetic parameters of the different formulations were calculated using WinNonlin software (version 4.0.1), using the trapezoid rule for calculation of AUC.

Absolute bioavailability of the oral different formulations was calculated by using the following equation:

$$\text{Absolute bioavailability}(\%) = \frac{AUC_{oral}}{AUC_{i.v.}} \times 100\%$$

The relative bioavailability of any oral formulation compared to the standard marketed formulation (CAPS) was calculated using the following equation:

$$\text{Relative bioavailability}(\%) = \frac{AUC_{oral}}{AUC_{caps}} \times 100\%$$

Stability Assessment of Oil Core at Different Experimental Conditions

The chemical stability of tacrolimus in argan oil/labrafil over long term storage at 37° C. at different experimental conditions was evaluated following the dissolution of 5 mg tacrolimus in 300 µl Argan oil:Labrafil 5:1 solution (AL SOL.). Various antioxidant excipients were also dissolved in the oil formulation as described in Table 6. Some of the formulations stored in well closed glass vials were flushed with nitrogen to ensure inert atmospheric conditions.

TABLE 6

Oil formulation composition of 1.66% tacrolimus

| Formulation | Type of antioxidant, % w/v from oil phase |
|---|---|
| AL SOL. 1 | Vitamin E 0.05 + $N_2$ |
| AL SOL. 2 | BHT 0.05, propyl gallate 0.05 + $N_2$ |
| AL SOL. 3 | BHT 0.05, propyl gallate 0.05 |
| AL SOL. 4 | $N_2$ |
| AL SOL. 5 | Neat oil formulation |

Absorption Studies in Mini-Pigs

Mini-pigs weighted 18-21 kg were used in this study. The absorption studies were carried out using oral administration of 1 mg of tacrolimus to each animal formulated either as a Prograf® gelatin capsule commercial product (Comm. Prod.), and the novel DDS gelatin capsule using different EUDRAGIT blend (Nov. DDS=Formulation 29).

Surgical Procedures:

All surgical and experimental procedures were reviewed and approved by the Animal Care and Use Committee of the Hebrew University (MD 117.04-3). Small pigs 18-21 kg in weight were used for all studies. Animals were fasted overnight; free access to a drinking water was permitted throughout the study. The following morning, the animals were anesthetized by isofloran (mask) for short period (10 min). During this period the animals were:

(1) dosed by oral, in the fasted state, with 1 mg per animal of tacrolimus formulated as Prograf® capsule commercial product, and as Nov. DDS;

(2) catheter was inserted to the jugular vein for blood sampling and was fixed on back of the pig. Blood samples (1 ml) were taken at 0, 15 min, 30 min and 1, 1.5, 2, 3, 4, 8, 12, and 24 hours and collected in heparin-containing tubes (the animal was conscious during the experiment).

The samples were immediately frozen at −20° C., and assayed for tacrolimus levels using PRO-Trac™ II ELISA kit (DiaSorin, USA).

Results and Discussion

Morphological Analysis

Figure 1B:
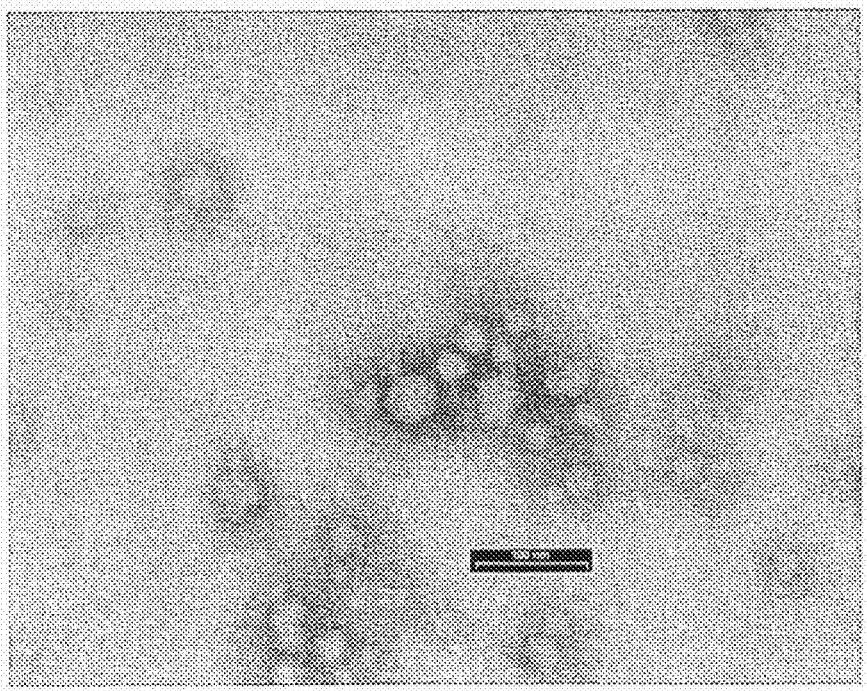
Figure 2A:
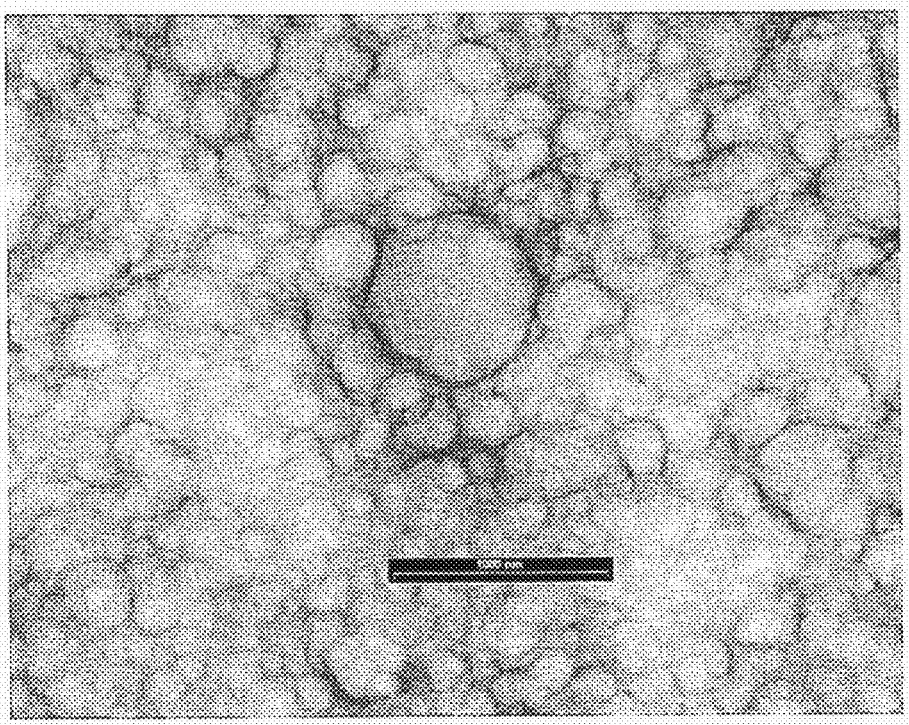
FIGS. 2A-2B are TEM micrographs of the nanocapsule formulation No. 29 with hydroxypropylmethylcellulose solution. The volume ratio of the acetonic solution to the water solution is 100:275. Bar represents 1000 nm in (FIG. 2A) and 100 nm in (FIG. 2B).
Figure 2B:
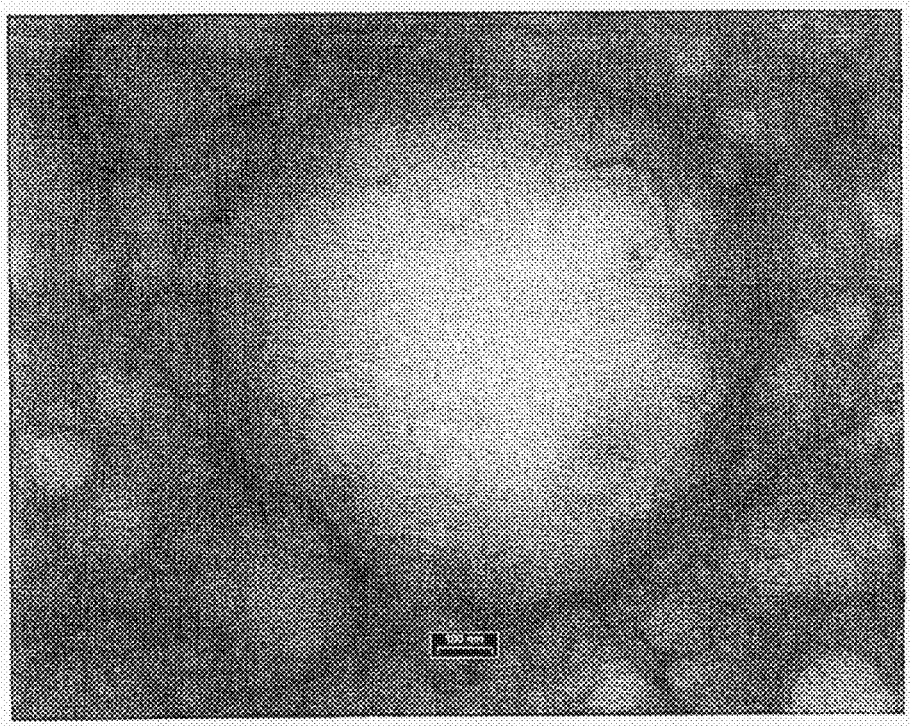

Surprisingly, when the water phase was slowly added to the organic phase (Table 2); first, the water dispersed in the oil phase, then, after the addition of a water volume estimated to be 15 ml of water in 100 ml of acetonic solution, an o/w emulsion was formed as evidenced by the rapid formation of opalescence in the dispersion medium. At this stage, the rapid diffusion of the internal acetone/ethanol phase towards the external aqueous phase occurred resulting in the deposition of the hydrophobic polymers at the o/w interface and formation of nanocapsules which consist of an oil core coated by the EUDRAGIT polymer blend as depicted in FIG. 1 where the final ratio of acetone solution to water was 100:75 v/v. It should be emphasized that under identical EUDRAGIT blend concentration but in the absence of oil, the EUDRAGIT phase separation phenomena and opalescence which reflected the separation of the polymers from the acetonic solution, occurred after 45 and 35 ml of water addition in formulation Nos. 29 and 30 respectively. This difference may be due to the different ratio of EUDRAGIT RS Poly(ethyl acrylate-co-methyl methacrylate-co-trimethylammonioethyl methacrylate chloride) 1:2:0.1) and EUDRAGIT L100-55 (Poly(methacylic acid-co-ethyl acrylate)) 1:1) in the blend between formulation 29 and 30. Apparently, when water is slowly added to the acetone:ethanol/oil phase comprising the labrafil surfactant which exhibits a low HLB value of 4, a transparent w/o micro-emulsion is formed and no phase separation is noted. Upon progressive and continuous water addition, at a certain hydrophilic:lipophilic volume ratio, an inverse o/w emulsion is spontaneously formed followed immediately by the displacement (diffusion) of the acetone and ethanol towards the external aqueous phase, leading to the deposition of the hydrophobic EUDRAGIT polymer blend at the o/w interface of the oil droplets resulting in the formation of the nanocapsule envelope around the argan oil core where the drug and surfactant are dissolved. At this stage where only 75 ml of water were added, the EUDRAGIT blend film around the nanocapsules is still partially hydrated and thin as noticed in FIGS. 1A and 1B. Upon further addition of 200 ml of 0.5% methylcellulose solution, a complete extraction of acetone and ethanol from the nanocapsules occurred and a more rigid and EUDRAGIT film is formed as can be deduced from the data presented in FIGS. 2A and 2B. Large nanocapsule aggregates are formed owing to the presence of the methylcellulose and to the high concentration of nanocapsules in the dispersion. The rigid polymer film around the oil droplets is distinct and can be easily identified as compared to the thin film noted in the nanocapsules visualized in FIGS. 1A and 1B.

Figure 3A:
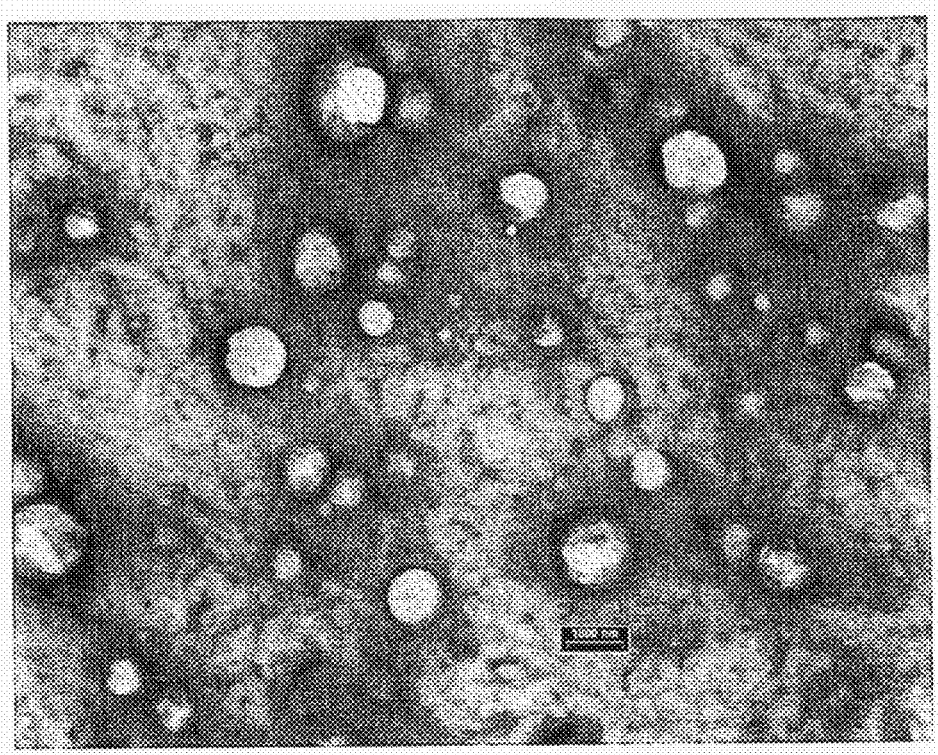
FIGS. 3A-3B are TEM micrographs of the nanocapsule formulation No. 30 without hydroxypropylmethylcellulose solution. The volume ratio of the acetonic solution to the water solution is 100:75. Bar represents 1000 nm, where
Figure 3B:
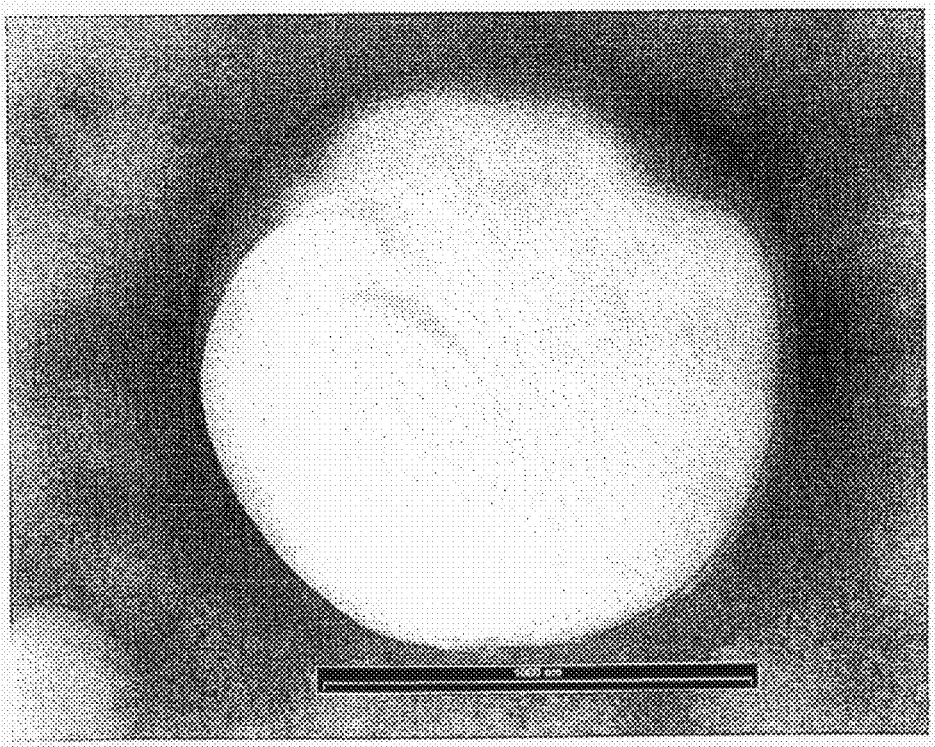
Figure 4:
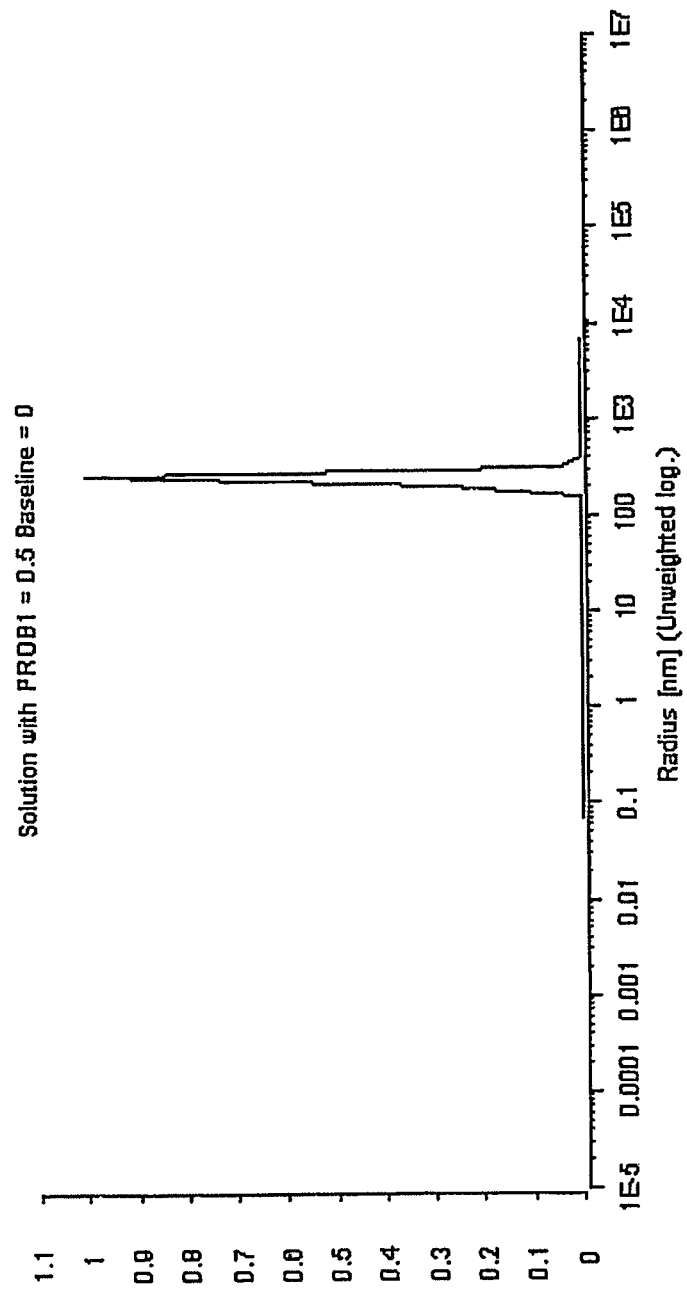
FIG. 4 shows particles size distribution before spray drying of formulation No. 29.

This was further confirmed when the formulation No. 30 was diluted with 75 ml of water without methylcellulose solution (i.e. 100:75, v/v). A more pronounced interfacial deposition of EUDRAGIT blend occurred and a rigid EUDRAGIT film the thickness of which was qualitatively estimated to be 30 nm was formed as shown in FIGS. 3A and 3B. Indeed, the solubility of this specific blend is smaller than the solubility of the EUDRAGIT blend in formulation 29 which separated later when at least 45 ml of water were added instead of 35 ml for formulation 30. No oil phase or oil droplets are detected using this approach as described in Table 2. The particle size distribution of the selected nanocapsule dispersion formulation No. 29 exhibited a narrow range with an average diameter of 479 nm (FIG. 4).

Figure 5A:
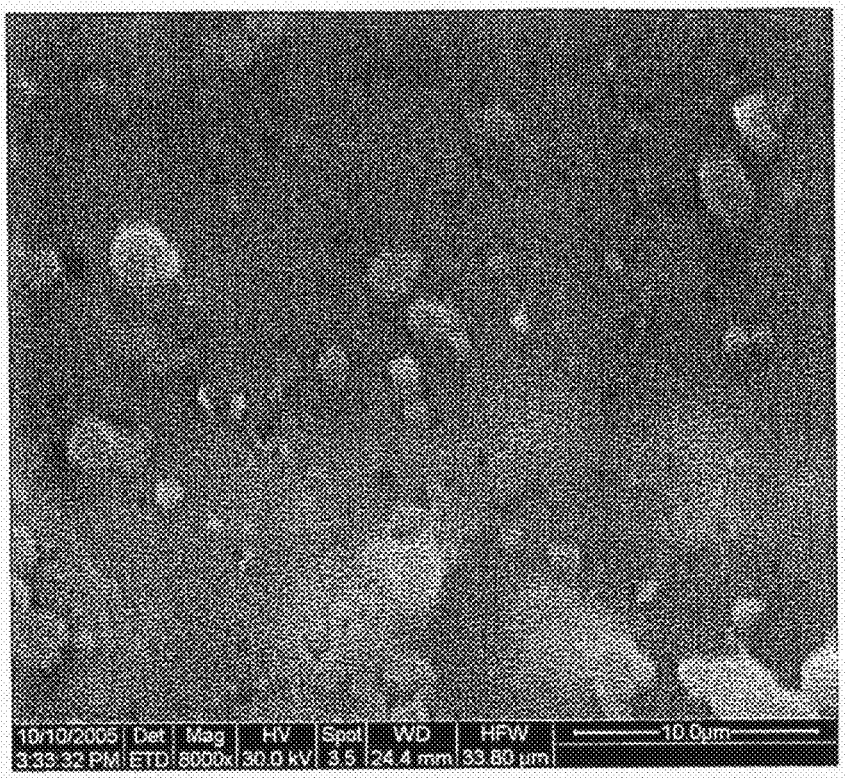
FIGS. 5A-5B are SEM micrographs of the nanocapsule formulation No. 29 before adding the hydroxypropylmethylcellulose solution (bar represents 10.0 μm FIG. 5A; 2.0 μm FIG. 5B).
Figure 5B:
Figure 6A:
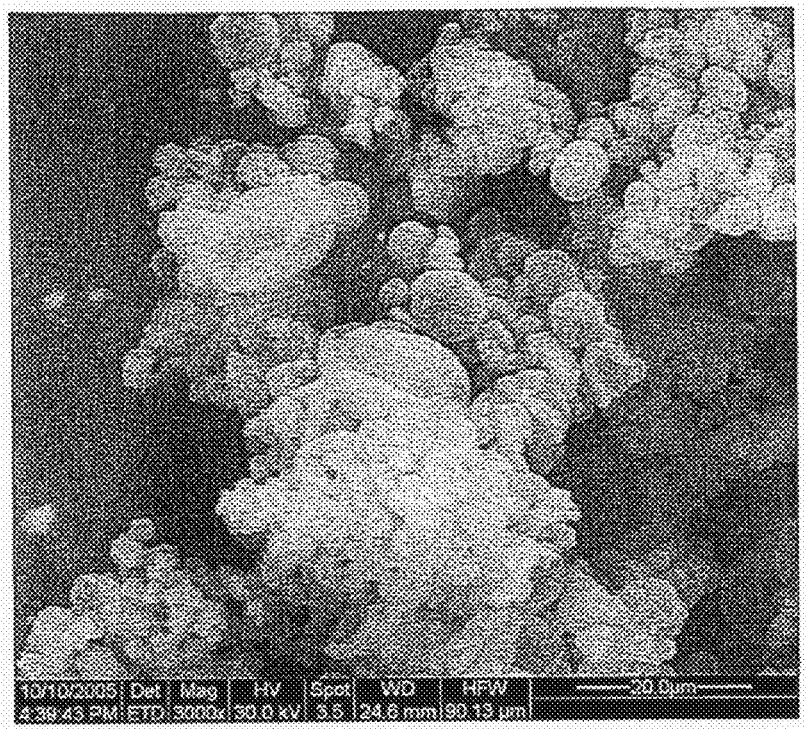
FIGS. 6A-6B are SEM micrographs of the nanocapsule formulation No. 29 with hydroxypropylmethylcellulose solution following spray drying (bar represents 20.0 μm FIG. 6A; 10.0 μm FIG. 6B).
Figure 6B:
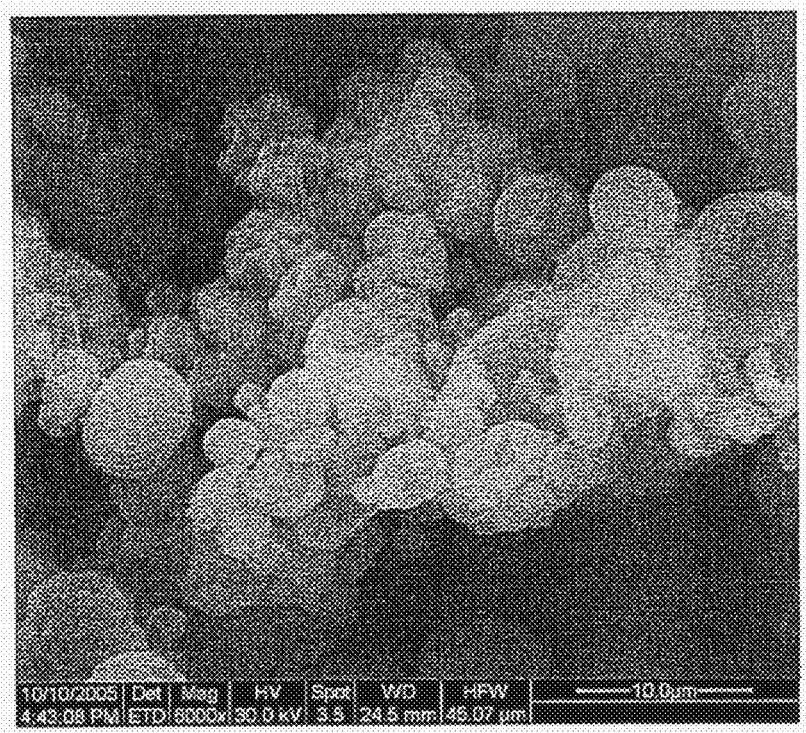
Figure 7A:
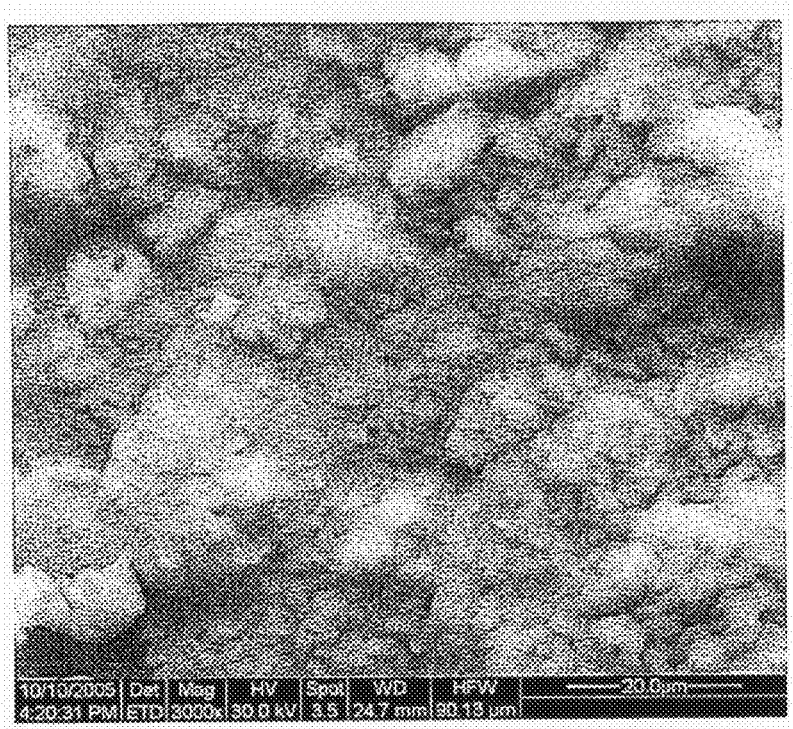
FIGS. 7A-7B are SEM micrographs of the nanocapsule formulation No. 29 following addition of hydroxypropylmethylcellulose solution and after 3 hr dissolution (bar represents 20.0 μm FIG. 7A; 10.0 μm FIG. 7B).
Figure 7B:
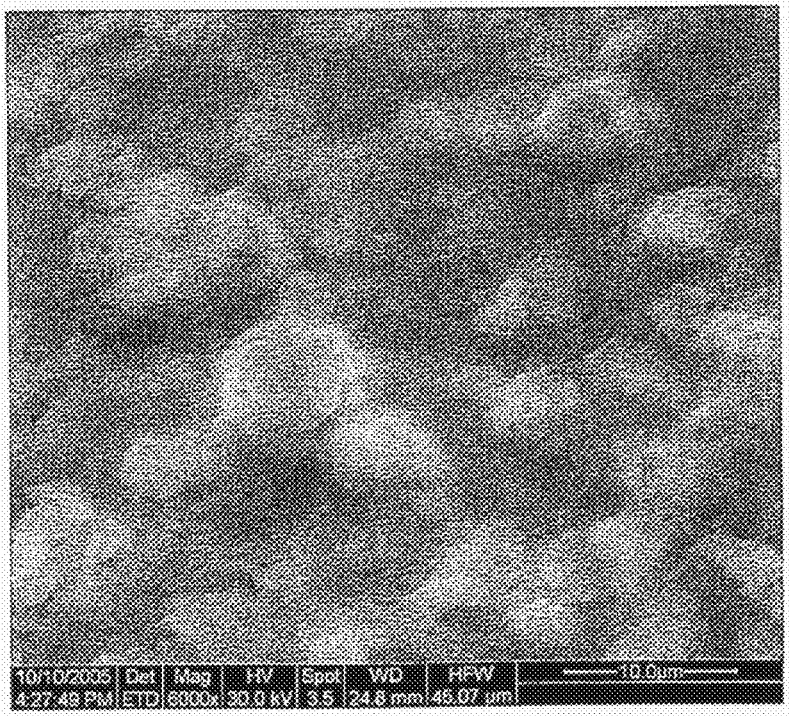
Figure 8A:
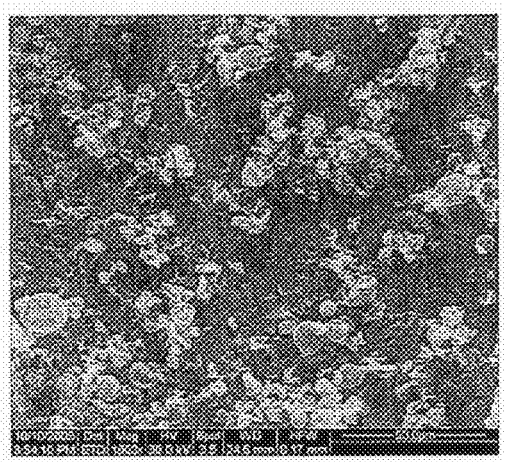
FIGS. 8A-8D are SEM micrographs of the nanocapsule formulation No. 30 following addition of hydroxypropylmethylcellulose solution and after spray drying (bar represents 50.0 μm FIG. 8A; 20.0 μm FIG. 8B; 10.0 μm FIG. 8C; 5.0 μm FIG. 8D).
Figure 8B:
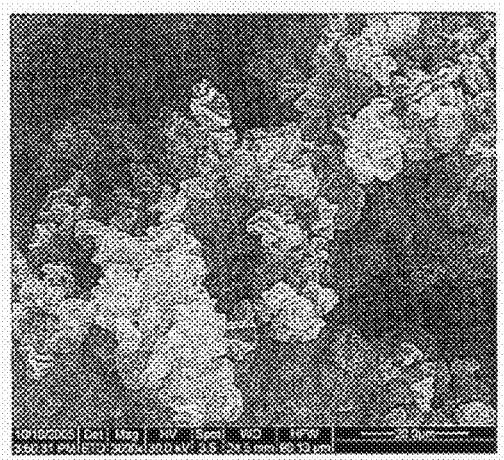
Figure 8C:
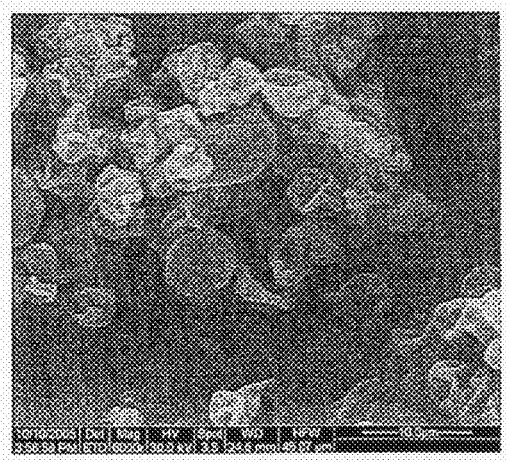
Figure 8D:
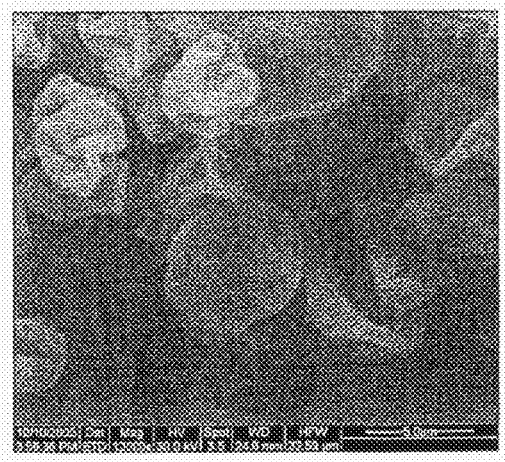
Figure 9A:
FIGS. 9A-9B are SEM micrographs of the nanocapsule formulation No. 30 following addition of hydroxypropylmethylcellulose solution and after spray drying and 3 h dissolution (bar represents 10.0 μm FIG. 9A; 5.0 μm FIG. 9B).
Figure 9B:

SEM analysis confirmed the previous TEM results and show individual nanocapsules formed following addition of 75 ml water in formulation 29 (FIGS. 5A and 5B). However, following addition of methylcellulose solution and spray drying, spherical microspheres (ranging qualitatively in size from 2-5 μm) forming small aggregates (ranging qualitatively in size from 10-30 μm) can be detected (FIGS. 6A and 6B). Furthermore, it was not possible to distinct any regular structural morphology following immersion of the spray dried aggregate in the release medium pH 7.4 over 3 h (FIGS. 7A and 7B). In fact the EUDRAGIT forming film blend in formulation No 29 comprised EUDRAGIT L 100-55 (Poly (methacylic acid-co-ethyl acrylate)) 1:1): EUDRAGIT RS Poly(ethyl acrylate-co-methyl methacrylate-co-trimethylammonioethyl methacrylate chloride) 1:2:0.1) 75:25. Eudragit EUDRAGIT L100-55 (Poly(methacylic acid-co-ethyl acrylate)) 1:1) is readily soluble above pH.5.5 while EUDRAGIT RS Poly(ethyl acrylate-co-methyl methacrylate-co-trimethylammonioethyl methacrylate chloride) 1:2:0.1) is insoluble irrespective of the pH. Thus, the primary methylcellulose coating and secondary nanocapsule EUDRAGIT blend coating are rapidly dissolved and no defined structure can be identified. However, it can be observed from the SEM analysis (FIGS. 8A-8D) that formulation No 30, following spray drying, elicited less aggregates and more spherical structures which are deflated as a result of vacuum. Furthermore, in FIGS. 9A and 9B, numerous nanocapsules can be detected within the microsphere void cores following immersion in release medium over 3 h evidencing the findings that the EUDRAGIT blend nanocapsule coating comprised of EUDRAGIT RS Poly(ethyl acrylate-co-methyl methacrylate-co-trimethylammonioethyl methacrylate chloride) 1:2:0.1): EUDRAGIT L 100-55 (Poly(methacylic acid-co-ethyl acrylate)) 1:1), 75:25, is more resistant to the aqueous release medium and should control the release of the encapsulated drug over time.

In Vitro Release Kinetic Evaluation

Figure 10:
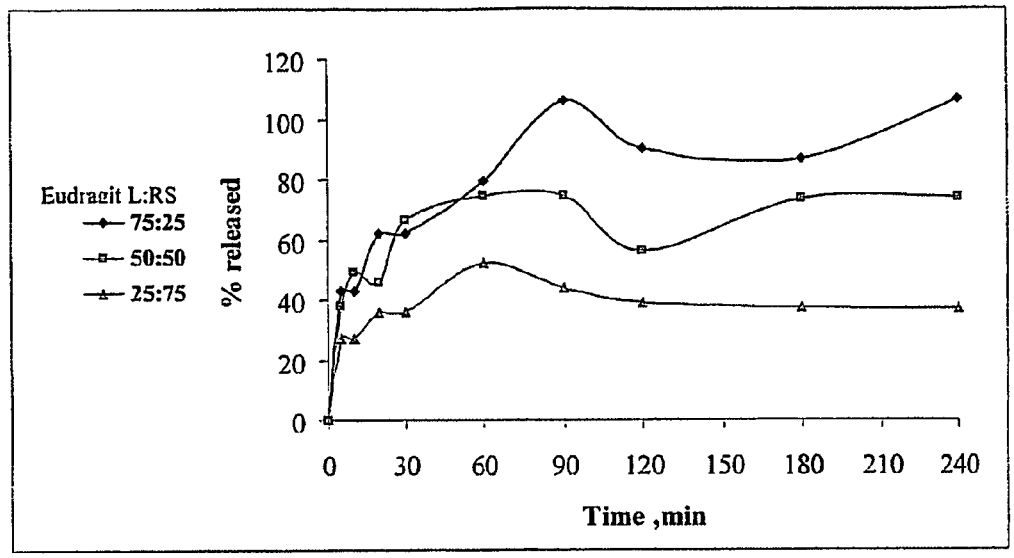
FIG. 10 is a graph showing DXPL release profiles from methylcellulose microspheres comprising nanocapsules with different EUDRAGIT(Poly(methacylic acid-co-ethyl acrylate) blend coatings.

The in vitro release data may suggest that the release of the agent from the microspheres may be controlled by variations in the polymer coating applied around the oil droplets. As can be noted from FIG. 10 the release profile of DXPL is faster with the EUDRAGIT L:RS, 75:25 than with the RS:L, 75:25, indicating that EUDRAGIT L is more readily permeable and elicited rapid release rates than EUDRAGIT RS Poly(ethyl acrylate-co-methyl methacrylate-co-trimethylammonioethyl methacrylate chloride) 1:2:0.1).

Figure 11:
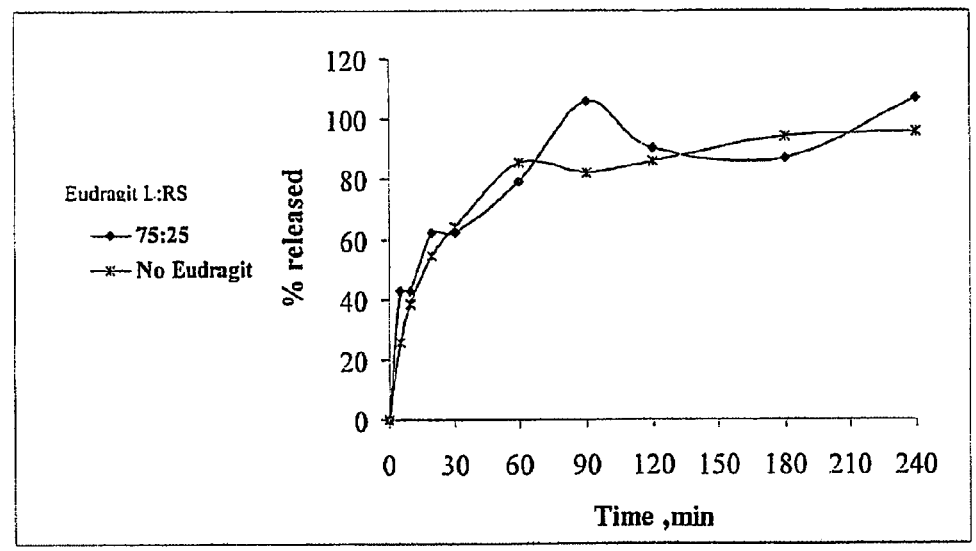
FIG. 11 is a graph showing DXPL release profiles from microencapsulated DXPL loaded EUDRAGIT nanocapsules and microencapsulated DXPL loaded oil in water emulsion.

FIG. 11 shows results where DXPL submicron emulsion without EUDRAGIT coating was spray dried under identical experimental conditions as the formulation No. 29. Both types of microspheres elicited similar release profiles. Instead of dissolved DXPL and DXPL loaded nanocapsule release, DXPL dissolved and small DXPL loaded oil droplets were released reflecting the same DXPL total released amount for both experiments. These findings suggest that the release kinetic experiments cannot differentiate between dissolved DXPL and DXPL incorporated into oil droplets or nanocapsules.

Stability Assessment of Tacrolimus Dissolved in the Nanocapsule Oil Core at Different Experimental Conditions It can be deduced from the data depicted in Table 7 that tacrolimus is not stable following one month storage at 37° C. when dissolved in an oil formulation even under nitrogen atmosphere and in the presence of various antioxidants unless formulated with BHT and propyl gallate and combined with nitrogen atmosphere.

Stability Evaluation of Microencapsulated Tacrolimus Nanocapsules Stored at Room Temperature The final dry formulation of microencapsulated tacrolimus nanocapsules was stored in well closed plastic containers at room temperature. Formulation No. 29 was assayed after 3 and 4 months and the tacrolimus content determined using HPLC was found to be 99 and 95% of initial, content respectively. The stability of the end product at room temperature is under continuous monitoring. The final selected end formulation will be subjected to accelerated stability tests in the near future.

TABLE 7

Evaluation of tacrolimus content in the oil core as a function of formulation parameters when stored at 37° C.

| Formulation | Antioxidant | 1 week % of initial content | 1 month % of initial content |
|---|---|---|---|
| AL SOL. 1 | Vitamin E + $N_2$ | 92.2 | 84.4 |
| AL SOL. 2 | BHT, propyl gallate + $N_2$ | 117.6 | 115.5 |
| AL SOL. 3 | BHT, propyl gallate | 99.7 | 82.0 |
| AL SOL. 4 | $N_2$ | 84.9 | 59.8 |
| AL SOL. 5 | None | 113.1 | 85.2 |

Absorption Studies in Rats

As previously mentioned, tacrolimus is associated with a markedly variable bioavailability and pharmacokinetics following oral administration. It was suggested that intrinsic jejunal permeability of tacrolimus is quite high. Regional dependency of tacrolimus permeability was also examined, and the studies revealed that tacrolimus permeability decreased dramatically in the ileum and colon compared to that in the jejunum. In that case, much of the tacrolimus variability appears to result from other factors such as P-glycoprotein (P-gp) efflux mechanisms or CYP3A metabolism effect which may be responsible for the observed regional dependency (5). Indeed, it was reported that the combined effects of CYP3A and P-gp on intestinal absorption and oral bioavailability are major barriers to oral drug delivery of tacrolimus [Kagayama A, et al., Oral absorption of FK506 in rats. Pharm Res. 10:1446-50 (1993)]. Attempts have been made to improve tacrolimus absorption by selectively transferring the drug into the lymphatic system by means of an o/w oleic acid emulsion (15). The authors administered orally the tacrolimus emulsion to rats at doses of 2 and 1 mg/kg and compared it to the commercial product. It was observed that reducing the dose from 2 mg/kg to 1 mg/kg decreased significantly the $C_{max}$ in the blood rat from 36.3±18.3 to 8.5±4.8 and from 32.1±9.6 to 6.0±2.2 ng/ml for the commercial and emulsion dosage forms respectively. Similar results were reported upon oral administration of tacrolimus in a dispersion dosage form to fed rats at doses of 1, 3.2 and 10 mg/kg which yielded $C_{max}$ values of 8.8±4.9, 11.6±5.3 and 40.2±19.4 ng/ml.

The current results show that an oral administration of the commercial product (CAPS) at a dose of 0.7 mg/kg elicited a $C_{max}$ of 1.1±0.8 ng/ml, well below the reported values clearly showing a significant influence of the administered dose on the $C_{max}$ value. Furthermore, the emulsion elicited a $C_{max}$ value of 2.2±0.46 ng/ml while the formulation No 29 elicited a $C_{max}$ value of 11.1±2.7 ng/ml as depicted in Table 8.

Figure 12:
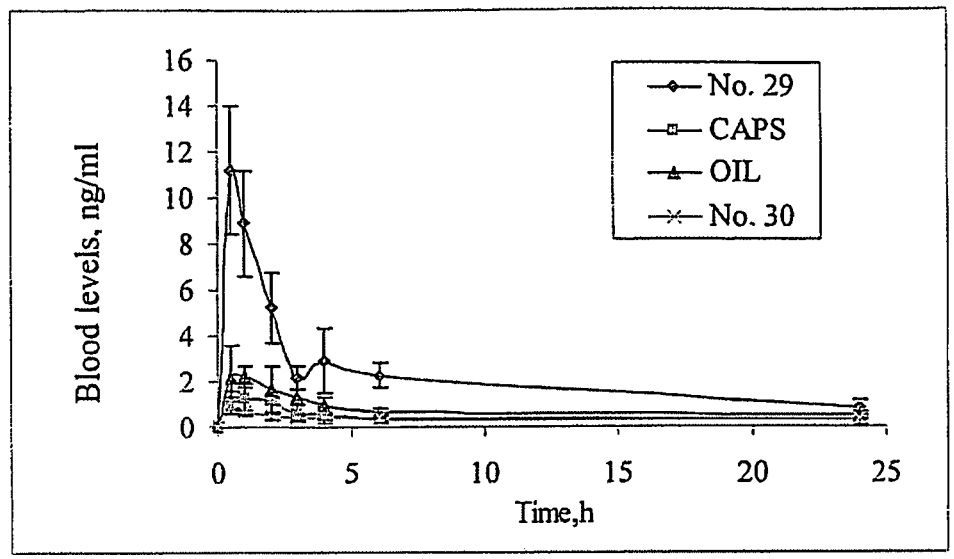
FIG. 12 is a graph showing tacrolimus systemic blood concentration after P.O. administration of different formulations to rats (mean±SD, n=6).
Figure 13:
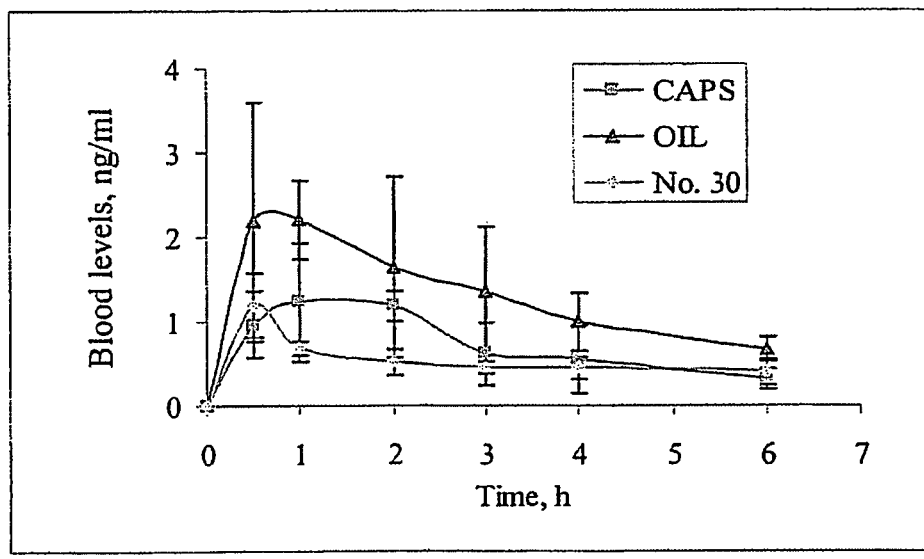
FIG. 13 is a graph showing tacrolimus systemic blood concentration after P.O. administration of different formulations to rats (mean±SD, n=6).

In addition, the absorption profile elicited by formulation 29 was significantly better than the profiles yielded by the emulsion and commercial product (FIG. 12). However, Formulation 30 did not elicit an enhanced release profile compared to formulation 29 (FIG. 13).

Figure 14:
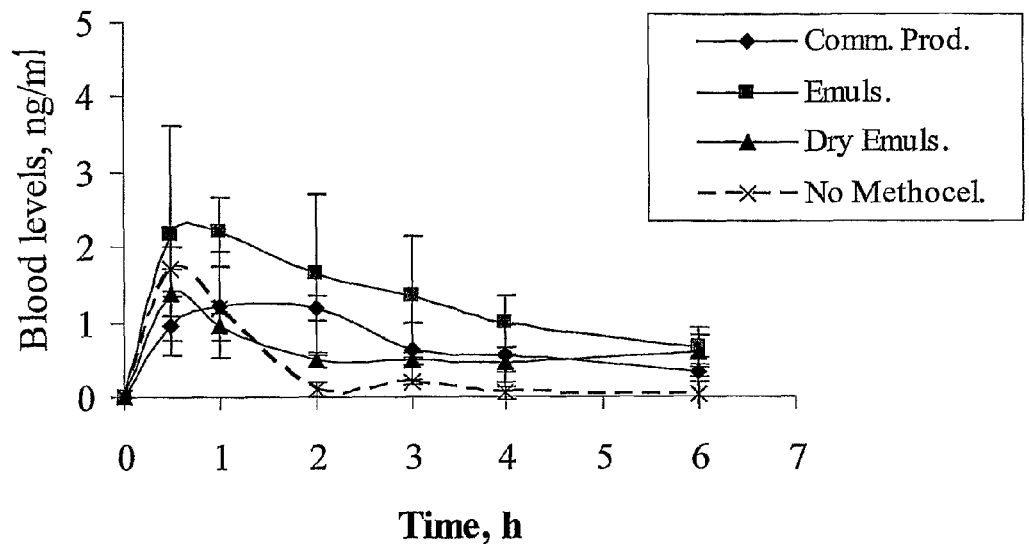
FIG. 14 is a graph showing tacrolimus blood levels following oral absorption of 0.7 mg/kg tacrolimus doses in various formulations (tacrolimus formulated either as a suspension of Prograf® capsule commercial product (Comm. Prod.), an emulsion (Emuls.), an emulsion embedded in the microspheres without EUDRAGITs but with hydroxypropylmethylcellulose (Dry Emuls.), without hydroxypropylmethylcellulose but with EUDRAGIT nanocapsules and lactose as a spray drying agent (No Methocel)).

In addition, tacrolimus blood levels following oral absorption of 0.7 mg/kg tacrolimus dosed in various formulations to rats (mean±SD, n=3-6, p>0.05). were determined (FIG. 14). Rat absorption studies were carried out using oral gavage, with 0.7 mg/kg (0.2 mg/rat) of tacrolimus formulated either as a suspension of Prograf® capsule commercial product (Comm. Prod.), an emulsion (Emuls.), an emulsion embedded in the microspheres without EUDRAGITs but with methyl cellulose (Dry Emuls.), without methyl cellulose but with EUDRAGIT nanocapsules and lactose as a spray drying agent (No Methocel).

Figure 15:
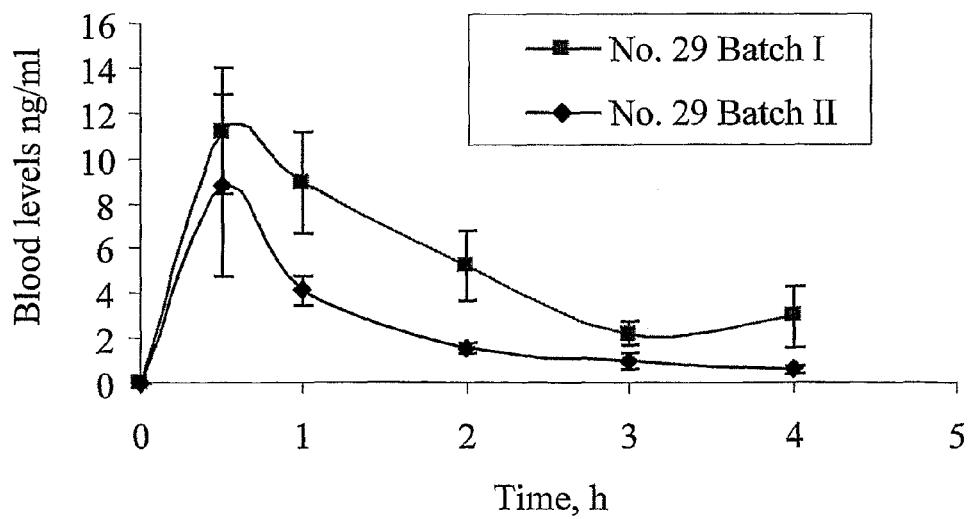
FIG. 15 is a graph showing tacrolimus systemic blood concentration after P.O. administration of two identical batches of formulation 29 to rats (mean±SD, n=6 for Batch I and n=3 for batch II), batch reproducibility evaluation.

In view of the lower performance of formulation 30, it was decided to evaluate the reproducibility of the manufacturing process of the microencapsulated tacrolimus loaded nanocapsules obtained in formulation 29. It can be deduced from the data presented in FIG. 15 that the absorption profiles elicited by Formulation 31 which is identical to Formulation 29 are close to the profiles yielded by Formulation 29.

Taking into consideration, the high variability of tacrolimus absorption, these findings suggest that the process parameters are well controlled and reproducible.

Figure 16:
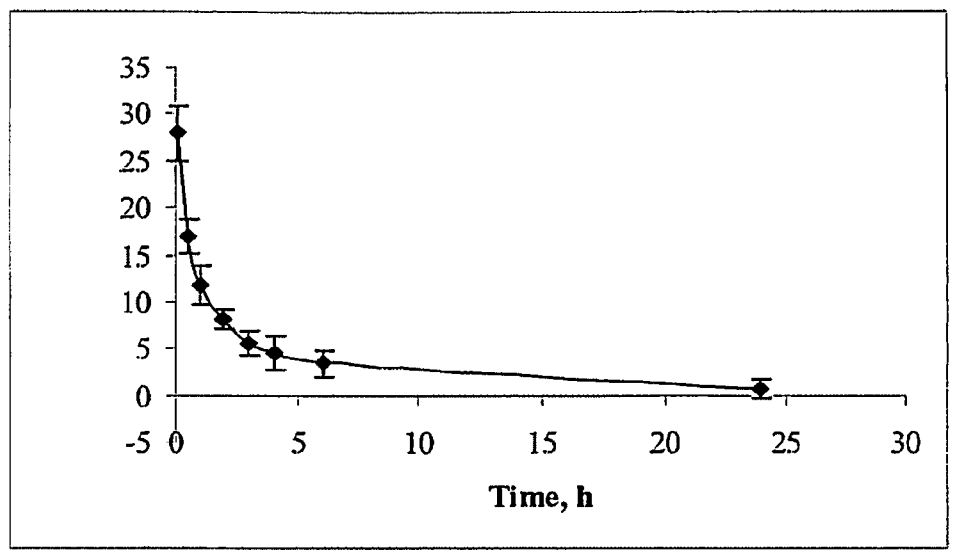
FIG. 16 is a graph showing tacrolimus blood levels following intravenous administration of a commercial Prograf® concentrate for infusion ampoule at a dose of 160 μg/kg to rats (mean±SD, n=5).

Further, It can be deduced from the data presented in FIG. 16 that apparently Formulation No 29 may have contributed to the liver bypass of tacrolimus and promote some lymphatic absorption of tacrolimus resulting in a more enhanced bioavailability compared to the commercial product.

Figure 17:
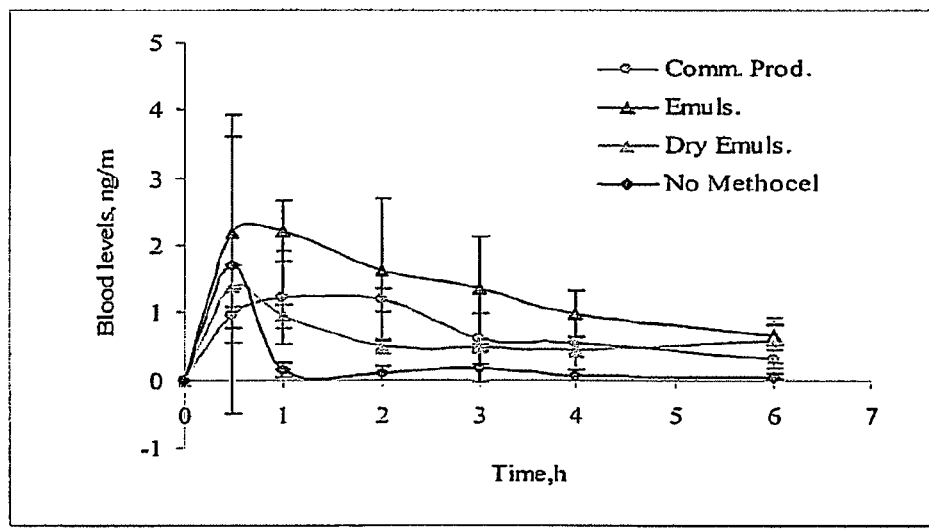
FIG. 17 is a graph showing tacrolimus blood levels following oral absorption of 0.7 mg/kg tacrolimus doses in various formulations to rats (mean±SD, n=3-6, p>0.05).

To calculate the absolute bioavailability of the oral formulation an intravenous pharmacokinetic study was carried and the data are presented in FIG. 17. The absolute bioavailability of the oral formulations were below 12% confirming the data already reported on the bioavailability of tacrolimus (Table 8). However, the results achieved with Formulation No 29 show that the bioavailability was increased by 490% with regard to the commercial capsule formulation as shown in Table 8 where the values of $AUC_{0-24}$ and $C_{max}$ are depicted for all the formulations. It should also be pointed out that the emulsion formulation increased the relative bioavailability by 210% as compared to the commercial product but elicited only 42.8% of the bioavailability of Formulation 29 as reflected from the respective $AUC_{0-24}$ values shown in Table 8. The improved oral absorption of tacrolimus by the actual microencapsulated nanocapsules (the microspheres of the invention) may be mediated by intestinal lymphatic uptake. The uptake of micro- and nanoparticles by the gastrointestinal epithelium is now a widely accepted phenomenon and has prompted investigators to focus on this route of delivery for labile molecules using microparticulate carriers (29).

TABLE 8

Pharmacokinetic parameters and bioavailability calculations

| Formulation | $C_{max}$ | AUC, ng/ml/hr | Absolute Bioavailability, % | Relative Bioavailability, % |
|---|---|---|---|---|
| Prograf® I.V. | — | 360 ± 24.6 | — | — |
| 29 | 11.1 ± 2.7 | 39.5 ± 21.6 | 11.0 | 490.2 |
| OIL (EMULS) | 2.2 ± 0.5 | 17.0 ± 9.5 | 4.7 | 210.6 |
| Prograf® Capsules | 1.1 ± 0.8 | 8.1 ± 3.5 | 2.2 | — |
| 32 | 1.4 ± 0.3 | 10.4 ± 5.4 | 2.8 | 125.8 |

The results presented in Table 8 show that the formation of nanocapsules is important for the performance of the delivery system. A simple emulsion cannot retain the tacrolimus within the oil core, resulting in a marked pre-systemic metabolism degradation of tacrolimus as clearly reflected by the results elicited by formulation 32 which is identical in contents to formulation 29 but without the Eudragit blend forming the nanocapsule coating wall.

In addition, histopathological preparates were taken from the rat duodenum, 30 minutes after an oral gavage of formulation No. 29. The preparates were examined by fluorescent microscope and nanocapsules were easily detected in various regions of the tissue. These findings suggest that the particles also undergo endocytosis into normal enterocytes.

Figure 18:
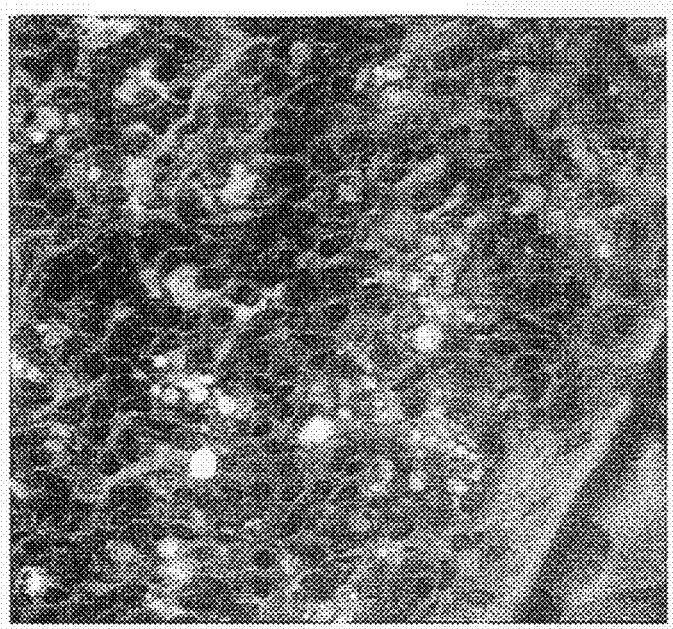
FIG. 18 is a fluorescent micrograph of histological section of rat duodenum 30 minutes after oral gavage of formulation No. 29, loaded with coumarin-6 as a marker.

On the other hand, a pronounced aggregation of nanoparticles was found in a Peyer's patch region (FIG. 18). The presence of a significant large number of nanocapsules in the Peyer's patch was thus suggested to be indicative of a potential escape from the P-gp efflux and their uptake by the lymph vessels allowing release of the capsule content in the systemic blood circulation bypassing the liver first pass effect.

Figure 19A:
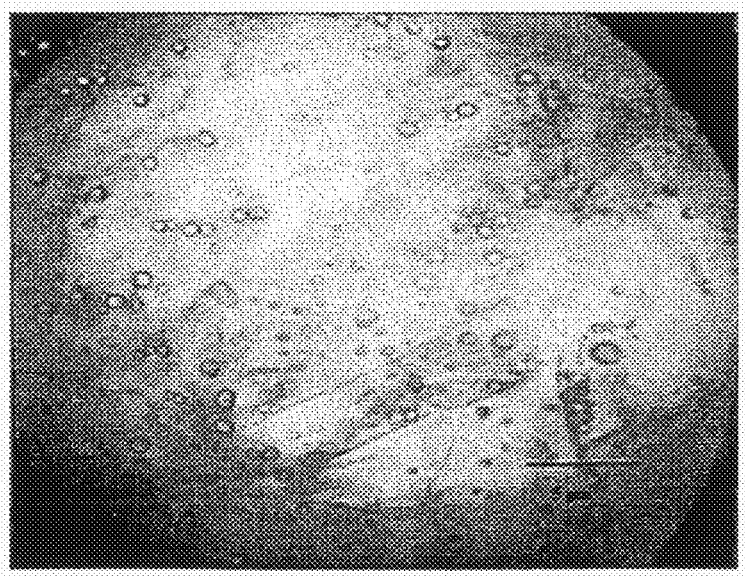
FIGS. 19A-19D are photomicrographs of dry (FIG. 19A) or impregnated (FIG. 19B-19D) empty nanocapsules prepared with EUDRAGIT L:RS (75:25) nanocapsule coating and hydroxypropylmethylcellulose matrix coating.
Figure 19B:
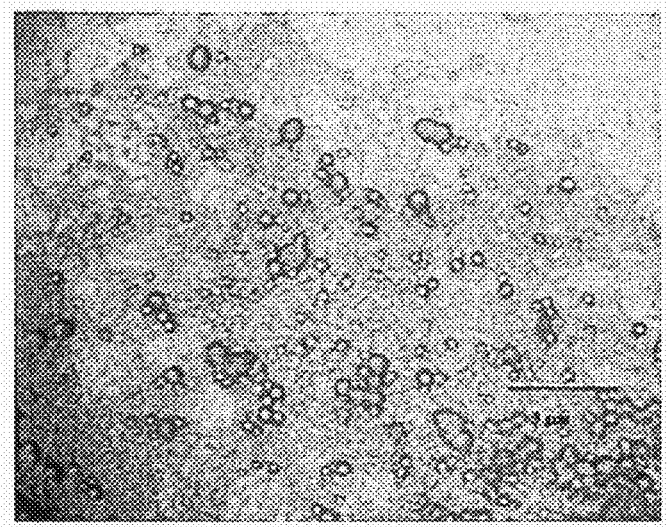
Figure 19C:
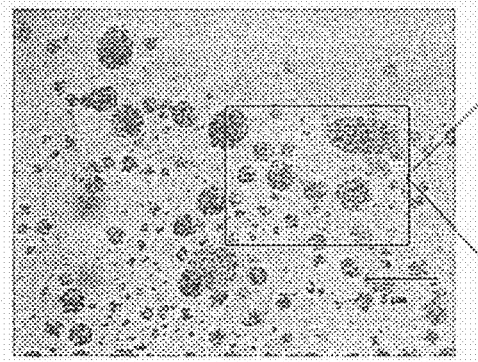
Figure 19D:
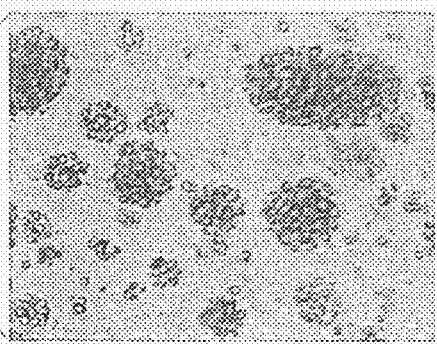
Figure 20:
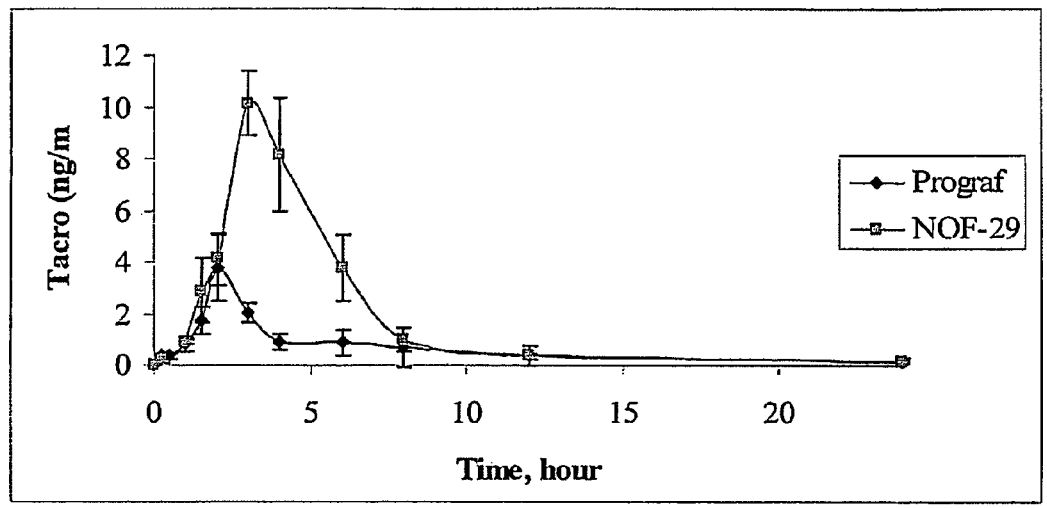
FIG. 20 is a graph showing tacrolimus blood levels following oral administration to mini pigs of 1 mg tacrolimus doses in a commercial formulation (Prograf) or in formulation No. 29 (Mean±SD, n=4).

In addition, different photomicrographs of the following were taken (FIGS. 19A-19D):
   dry microencapsulated empty nanocapsules prepared with Eudragit L:RS (75:25) nanocapsule coating and methylcellulose matrix coating (FIG. 19A);
   impregnated microencapsulated empty nanocapsules prepared with Eudragit L:RS (75:25) nanocapsule coated and methylcellulose matrix coating following 3 minutes incubation with phosphate buffer (pH 7.4) (FIG. 19B);
   impregnated microencapsulated empty nanocapsules prepared with Eudragit L:RS (75:25) nanocapsule coated and methylcellulose matrix coating following 5 minutes incubation with phosphate buffer (pH 4.8) (FIGS. 19C and 19D, FIG. 19D being the enlargement of a section from FIG. 19C).

The results presented in Table 8 show that the formation of nanocapsules is important for the performance of the delivery system. A simple emulsion cannot retain the tacrolimus within the oil core, resulting in a marked pre-systemic metabolism degradation of tacrolimus, as is clearly reflected by the results elicited by formulation 32 which is identical in contents to formulation 29 but without the EUDRAGIT blend forming the nanocapsule coating wall.

Without being bound by theory it was thus hypothesized that the improved oral absorption of an active agent by the microencapsulated nanocapsules is mediated by intestinal lymphatic particle uptake.

This is also evident from results obtained when formulations identical in content to Formulation No. 29, without the EUDRAGIT polymer nancapsule coating did not elicit an increase bioavailability as noted in FIG. 17 (Emul. and dry Emuls.) and Table 8 above.

Further, without being bound by theory, it was suggested that the delivery system in accordance with the invention may not only promoted lymphatic uptake, but also escape the pre-metabolism degradation and the P-gp efflux. The normal emulsion, although improved bioavailability as compared to the commercial product but not to the same extent as formulation 29, probably as a result of partitioning of tacrolimus in the GI (gastro-intestinal) fluids prior to its uptake by the enterocytes.

Thus, the delivery system of the invention may be preferably applicable for the delivery of various active agents which act or are considered as P-gp efflux substrates.

Further, the above presented findings showed that the dry emulsion, which resembles formulation No. 29 but without the EUDRAGIT polymer nanocapsule coating, was unable to retain the tacrolimus in the oil core in the GI fluids, resulting in a poorer bioavailability than the commercial product.

Yet further, the EUDRAGIT Nanocapsules without the Methocel did not elicit marked blood levels indicating that the actual nanocapsule coating was unable to retain tacrolimus under the present experimental conditions, and could not contribute to prevent tacrolimus efflux.

These findings have been confirmed by a 4 mini-pig cross over animal experiment. The results presented in FIG. 19 and in Table 9 below show that the delivery system of the invention, as exemplified by formulation 29 elicited 2.4 times higher drug levels contributed by the liver bypass of tacrolimus resulting in an enhanced bioavailability compared to the commercial product (Prograf®).

TABLE 9 pharmaceokinetic parameters and bioavailability calculations in mini-pigs (Mean ± SD, n = 4)

| Formulation # | AUC | $t_{1/2}$, h | $T_{max}$, h | $C_{max}$ (ng/ml) | Relative Bioavailability, % |
|---|---|---|---|---|---|
| No. 29 | 44.0 | 7.48 | 3 | 10.14 | 243.5 |
| Prograf ® | 18.06 | 9.11 | 2 | 3.76 | 100.0 |

It is clear from the results presented in the absorption studies in mini-pigs that relative bioavailablility reached by the drug delivery system of the invention was 2.4 times greater than the tested formulation.

In the present invention, in view of the overall results presented a plausible mechanistic explanation how the novel drug delivery system enhances significantly drug oral absorption may thus involve, without being bound by theory, (a) an endocytotic uptake—particles absorbed by intestinal enterocytes through endocytosis (particles size<500 nm); (b) a lymphatic uptake—particles adsorbed by M cells of the Peyer's patches (particle size<5 µm) and (c) an enhanced adhesion of the micropsheres and nanocapsules to the intestinal epithelium elicited by the adequate bioadhesive hydroxypropylmethylcellulose coating, resulting, overall in a marked improvement of the absorption into the intestinal cells due to the ability of escaping from the multi-drug resistance pump proteins.

Example 2

PLA Containing Nanocapsules Accommodated in Microcapsules (NOF-PLA)

Materials and Methods

Unless otherwise stated, the materials and methods are as provided in Example 1. Further, unless, otherwise stated, METHOCEL E4M refers to hydroxypropylmethylcellulose.

Preparation of NOF-PLA Formulations:

Poly lactic acid (Mw=10,000 daltons), LABRAFIL 1944 CS, Oleic acid and tacrolimus were dissolved into 100 ml of Acetone solution (oil phase). Water (75 ml) was added (within 2 minutes) to the oil phase to form a dispersion. The water phase was added to the acetone/organic phase leading first to the formation of a w/o microemulsion which upon continuous water addition yields an inverse o/w emulsion resulting in the formation of nanocapsules following displacement of the dipolar solvents. To the dispersed solution, a 200 ml of 0.5% of Methocel E4M and 0.35% of EUDRAGIT L100 55 (Poly(methacylic acid-co-ethyl acrylate)) 1:1) solution at pH=6.5 were added prior to the spray drying procedure. The Methocel E4M, EUDRAGIT L100 55 (Poly(methacylic acid-co-ethyl acrylate)) 1:1) and last water portion were added only after nanocapsule formation.

The composition of the formulation is as follows:

| # | Material Name | Amount | Unit |
|---|---|---|---|
| 1 | Acetone | 100 | ml |
| 2 | Poly lactic acid (Mw = 10,000) | 0.1 | g |
| 3 | EURAGIT L100-55 (Poly(methacyclic acid-co-ethyl)) 1:1) | 0.75 | g |
| 4 | Oleic acid | 0.5 | ml |
| 6 | Labrafil M 1944 CS | 0.1 | ml |
| 7 | Tacrolimus | 20 | mg |
| 8 | DD water | 75 | ml |
| 9 | Methocel E4M | 1 | g |
| 10 | DD water | 200 | ml |

Microencapsulation of the Tacrolimus Nanocapsules by Spray Drying Method

The thus formed suspension was spray-dried with a Buchi mini spray-drier B-190 apparatus (Flawil, Switzerland) under the following conditions: inlet temperature 160° C.; outlet temperature 100° C.; aspiration 50%; feeding rate of the suspension was 2.5 ml/min. the powder was collected in the cyclone separator and the outlet yield was calculated.

Drug Content

The total amount of the tacrolimus in the powder was analyzed by dissolving the sample in 5 ml of PBS. After the polymer was dissolved, 1 ml of acetonitrile (ACN) was added and the mixture was stirred (100 rpm) for 1 hr. Thereafter, 3 ml of ethyl acetate were added and the mixture was stirred vigorously and centrifuged at 4000 rpm for 5 minutes.

The extraction of tacrolimus by ethyl acetate was repeated three times to ensure total removal of the drug from the mixture. The different ethyl acetate layers (upper layer) were transferred to a clean tube and evaporated under air to dryness. The combined residues were dissolved in 1 ml of ACN, and 50 µl were injected into HPLC under the following conditions: Mobile phase—Acetonitrile 100%, Flow rate—0.5 ml/min, Wavelength—213 nm, Column—LiChrospher® 100 RP-18 (5 µm), 4/120 mm. A calibration curve constructed from tacrolimus concentrations ranging between 10 to 250 µg/ml yielded a linear correlation.

The tacrolimus incorporation yield was calculated by the following equation:

$$\text{Drug yield}(\%) = \frac{\text{Amount of the drug detected}}{\text{Amount of the drug incorporated}} \times 100\%$$

The calculated tacrolimus content yield was thus 93.8%. The calculated tacrolimus content was equal to 7.3 mg/g powdered formulation.

Absorption Studies in Rats

The study was approved by the local ethical committee of laboratory animal care in accordance with the rules and guidelines concerning the care and use of laboratory animals MD 104.01-3. Sprague Dawley rats weighting 300-325 g were used in this study. The animals were housed in SPF conditions. The animals were dosed by oral gavage, with 0.2 mg/rat of tacrolimus formulated either as a suspension of Prograf® capsule content (2 animals) or as NOF-PLA (3 animals). In a second set of experiments 5 animals were tested (3 rats for the Prograf group and 2 for NOF-PLA).

Blood samples (100-150 µL) were taken from the rat tail at 0, 30 min and 1, 1.5, 2, 3, 4, 6 and 24 hours. The blood samples were collected in heparin containing tubes. The samples were immediately frozen at −20° C. and assayed for tacrolimus levels using PRO-Trac™ II ELISA kit (DiaSorin, USA) following the protocol suggested by the company. This ELISA method is well accepted in clinical practice and is able to detect accurately tacrolimus blood levels from 0.3 to 30 ng/ml.

Results

Figure 21:
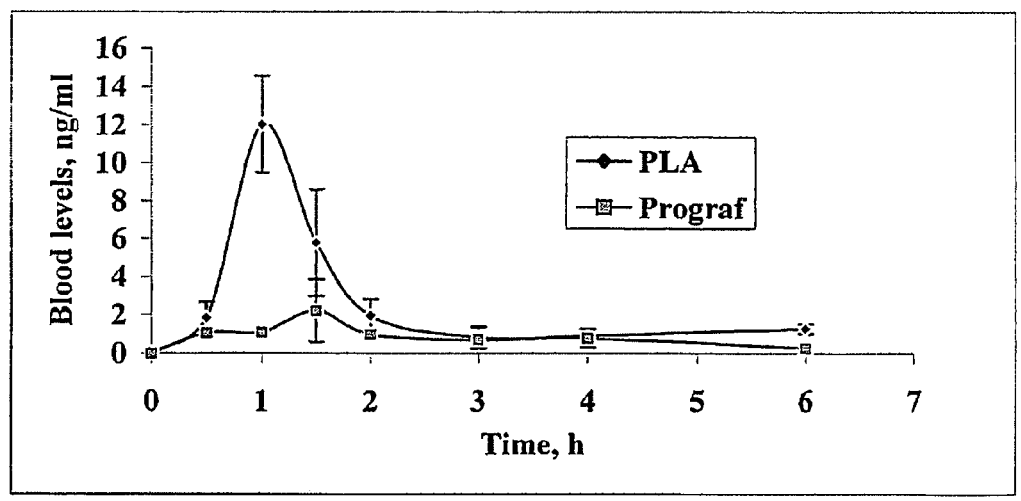
FIG. 21 is a graph showing tacrolimus blood levels following oral administration of 0.7 mg/kg tacrolimus dosed in the commercial formulation Prograf and in NOF-PLA formulation. (N=2-3).

The results are presented in FIG. 21. as shown the microencapsulated PLA nanocapsules elicited a much higher absorption profile than the commercial product, Prograf®.

Example 3

In Vitro Stability, Uptake in Caco-2 Cells and Transport Through Intestinal Membrane of Tacrolimus in Various Formulations Materials and Methods Materials Poly(ethyl acrylate, methyl methacrylate, trimethylammonioethyl methacrylate chloride) 1:2:0.1 (Eudragit® RS) and Poly(methacrylic acid, Ethyl acrylate) 1:1 (Eudragit® L1000-55) were purchased from Rohm (Dramstadt, GmbH, Germany). Hydroxypropylmethylcellulose (Methocel E4M Premium) was obtained from Dow Chemical Company (Midland, Mich., USA), Argan Oil was purchased from Alban-Muller (Vincenny, France), oleoyl polyoxylglycerides (Labrafil M 1944 CS) was kindly donated by Gattefosse (St. Priest, France), Tacrolimus (as monohydrate) was purchased from Concord Biotech Limited (Ahmedabad, India). Other chemicals and solvents were of analytical reagent grade and double-distilled water was used throughout the study. The commercial tacrolimus capsule product, Prograf® manufactured by Fujisawa Ltd. UK was purchased from a retail pharmacy (Batch number—5C5129B).

Preparation of the Nanocapsules

The primary nanocapsules were first prepared by dissolving in a solution of 95 ml of acetone and 5 ml of absolute ethanol, the following compounds: 500 mg of argan oil, 100 mg of oleoyl polyoxylglycerides, 250 mg of EUDRAGIT RS Poly(ethyl acrylate-co-methyl methacrylate-co-trimethylammonioethyl methacrylate chloride) 1:2:0.1), 750 mg of EUDRAGIT L and 20 mg of tacrolimus when needed. Then, purified water was added to the organic phase at a constant rate of 20 ml/min using stepdos 03RC pump (KNF Foldos, Sursee, Switzerland). An o/w emulsion was formed as evidenced by the rapid formation of opalescence in the dispersion medium. In some of the formulations, samples were withdrawn at 10, 20, s and 1, 2, 3, 4 min and examined by optical microscopy using an Olympus BX 40 light microscope (Olympus, Tokyo, Japan) at X 200 magnification and a Sony DXC-3900 video camera (Sony Corporation Tokyo, Japan). Nanocapsule size measurements for each sample were carried out utilizing the ALV sizer as detailed below. Preliminary formulations were prepared and evaluated by varying the process parameters including the blend ratio of the EUDRAGITs. An optimal formulation with a specific Eudragit blend ratio was selected for further studies: EUDRAGIT L: EUDRAGIT RS Poly(ethyl acrylate-co-methyl methacrylate-co-trimethylammonioethyl methacrylate chloride) 1:2:0.1) 750:250 (3:1). A formulation consisting of the identical oil core phase (same concentrations) without the wall coating polymers was also prepared and defined herewith as the "emulsion".

Microsphere Preparation

The microspheres were formed by microencapsulating the tacrolimus loaded nanocapsules using the spray drying technique. Once the nanocapsules were formed, 200 ml of 0.5% hydroxypropylmethylcellulose (HPMC) solution was added to the dispersed solution, prior to the spray drying procedure. The suspension was spray-dried with a Buchi mini spray-drier B-190 apparatus (Flawil, Switzerland) under the following conditions: inlet temperature 180° C.; outlet temperature 113° C.; aspiration 50%; feeding rate of the suspension was 2.5 ml/min. The powder was then collected in the cyclone separator and the outlet yield was calculated. The formulations with the EUDRAGIT blend ratios of L:RS of 3:1 were denominated N of −29. All the batch formulations were triplicated.

In-Vitro Stability of Tacrolimus in Rat Intestinal Juice (pH 6.5)

The following solutions were added sequentially to a test tube: 300 µl of freshly thawed intestinal juice, 60 µl of 0.6 M phosphate buffer, pH 6.5 (the pH of the mixture of intestinal juice) and 25 µg/ml of tacrolimus in various formulations (up to 1.5 ml). The mixtures were stirred and incubated at 37° C. over time. At given time intervals of 5, 10, 20, 30, 45, 60, 90 and 120 min, the samples were withdrawn from the incubation, mixed with 150 µl of 0.5 M hydrochloric acid and 2 ml of ethyl acetate. The resulting mixtures were stirred vigorously and centrifuged at 4000 rpm (equivalent to 3000 g) over 10 min. The extraction of tacrolimus by ethyl acetate was repeated three times to ensure total removal of the drug from the mixtures. The different ethyl acetate layers (upper layers) were transferred to clean tubes and evaporated under nitrogen to dryness. The combined residues were dissolved in 1 ml of acetonitrile, and 50 µl were injected in the HPLC under the following conditions: Mobile phase Acetonitrile 100%, Flow rate 0.5 ml/min, Wavelength—213 nm, Column—LiChrospher® 100 RP-18 (5 µm), 4/120 mm.

Results

A calibration curve constructed from tacrolimus concentrations ranging between 3.9 to 250 µg/ml yielded a linear relationship. The detection limit of tacrolimus was found to be 3.9 µg/ml.

Figure 22:
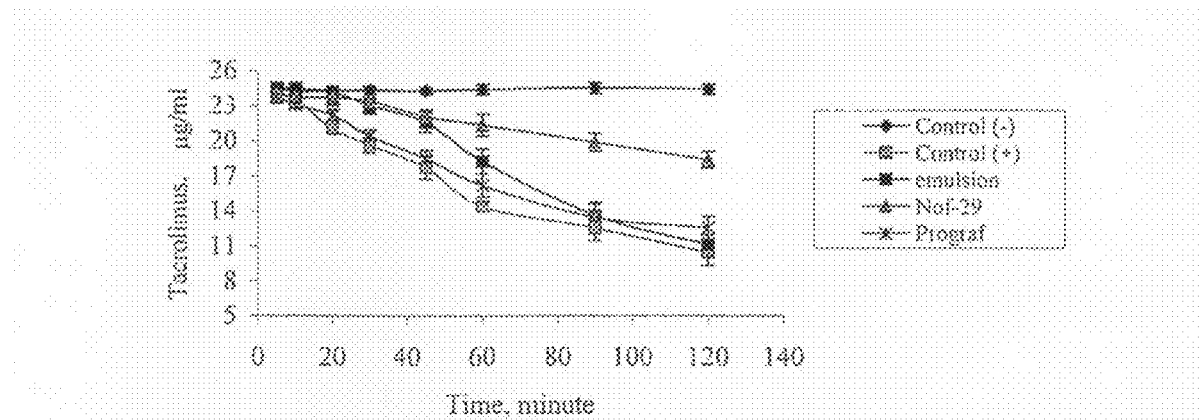
FIG. 22 is a graph showing tacrolimus stability in rat intestinal juice diluted with PBS (1:5 v/v, (PBS pH 6.5) as a function of time.

FIG. 22 shows that tacrolimus incubated only with PBS at pH 6.5 (Control (−)) remained intact and no degradation could be observed over 120 min incubation.

However, upon addition of intestinal juice (Control (+)), a rapid degradation occurred reducing the initial concentration by at least 50%. The formulation of tacrolimus in an emulsion or the commercial product Prograf did not protect tacrolimus from the enzymatic degradation in the intestinal juice whereas the microencapsulation of the tacrolimus loaded nanocapsules [Nof-29] elicited a marked enzymatic protection since only 20% of the initial tacrolimus concentration was decomposed.

Without being bound by theory, it seems that tacrolimus is slowly released from the double walled nanoparticulate delivery system and only the portion of drug released was subject to enzymatic degradation as expected. These results demonstrated that the dosage form of the present invention is able to protect significantly the sensitive drug from the enzymes present in the intestinal juice.

Caco-2 Uptake Study

Caco-2 monolayers (passage 73) were grown in Dulbecco's modified Eagle's medium supplemented with 10% fetal bovine serum, 1% L-glutamine, 1% nonessential amino acids, and 5% antibiotic-antimycotic solution at 37° C. in humidified air, 5% $CO_2$ atmosphere. The culture medium was first replaced after 72 h and every 48 h thereafter. The uptake studies were conducted with monolayers between 8 to 10 days in culture. All diffusion experiments were performed over 1 h at 37° C. Prior to the experiments, the culture medium was replaced with transport medium and cell monolayers were subsequently equilibrated for 30 min at 37° C. before the uptake study. Transport medium was Hanks buffer composed of 136.89 mM NaCl, 5.36 mM KCl, 0.34 mM $Na_2HPO_4$, 0.44 mM $KH_2PO_4$, 0.41 mM $MgSO_4$ $7H_2O$, 19.45 mM glucose, 1.26 mM $CaCl_2$, 0.49 mM $MgCl_2.6H_2O$, 4.17 mM $NaHCO_3$, 10 mM HEPES, and the pH was adjusted to 7.4. At the end of the experiments, the transport medium (1.5 ml) was withdrawn to a clean tube to determine the tacrolimus levels in HPLC. The cell monolayer was washed 3 times with 1 ml Hanks solution and combined with the transport medium. As for the cell monolayer in the wells, 1.5 ml of 1% SDS was administered into each well to undergo lysis of the cell monolayer. The lysate was collected in clean tube and tacrolimus was determined by HPLC as described above. When verapamil, a well-known CYP3A substrate and P-gp inhibitor (C. U. Wu and L. Z. Benet. Predicting drug disposition via application of BCS: transport/absorption/elimination interplay and development of a biopharmaceutics drug disposition classification system. *Pharm. Res.* 22: 11-23 (2005) was used, the concentration in the medium was 150 μg/ml and the Caco-2 cells were pre-incubated with the verapamil solution 30 min prior to the transport experiments.

Two separate and independent sets of cell culture experiments were carried out with similar tacrolimus formulations but different combinations to verify either the reproducibility and efficiency of Nof-29 or the effect of the blank Nof-29 formulation on the P-gp pump activity. The experiments were quadruplicated. The P-gp expression of the Caco-2 cells was validated using monoclonal antibody C219 directed against the P-gp according to the technique described by Schrickx and Fink-Gremmels (J. Schrickx and J. Fink-Gremmels. P-glycoprotein-mediated transport of oxytetracycline in the Caco-2 cell model. *J. Vet Pharmacol. Therap.* 30: 25-31 (2007). Caco-2 cells were fixed in paraformaldehyde (3.6% in PBS) for 15 min and treated with 0.1 M glycine for 5 min. After washing three times they were permeabilized with Triton X-100 (0.1%, w/v) for 15 min and washed again three times. For labeling with antibodies, the sandwich technique was used. Preparations were incubated for 1 h with the primary antibody (1:40), i.e., the specific anti P-gp (C219) purchased from Alexis Biochemicals (San Diego, USA). As a secondary antibody, Rhodamine-labeled anti IgG (1:50) was applied for 1 h. After washing again (three times), the cells were mounted in a mixture of 7 mL of glycerol 100%, 3 mL of 0.1 Tris-HCl, pH 9.5, and 0.5 g of n-propyl gallate. Immunohistochemistry images were taken by Olympus 1X71 microscope using Olympus ×40 lens magnification.

The apparent permeability ($P_{app}$, cm/s) was calculated according to the following equation described by Schrickx and Fink-Gremmels (J. Schrickx and J. Fink-Gremmels. P-glycoprotein-mediated transport of oxytetracycline in the Caco-2 cell model. *J. Vet Pharmacol. Therap.* 30: 25-31 (2007).

Results

Monolayers of differentiated Caco-2 cells show morphological and biochemical similarity to normal intestinal enterocytes, and they develop effective tight junctions. Thus, Caco-2 cell monolayer is considered an established model to investigate the mechanisms involved in oral absorption including the effect of the P-gp pump. The P-gp expression of the actual Caco-2 monolayer was evidenced (data not shown) using the validated monoclonal antibody C219 technique. It can be seen as compared to the control that the Caco-2 cells elicited marked fluorescence demonstrating the affinity binding of the secondary antibody to the Caco-2 cell membranes as a result of the recognition of the P-gp by the C219 antibody.

Figure 23A:
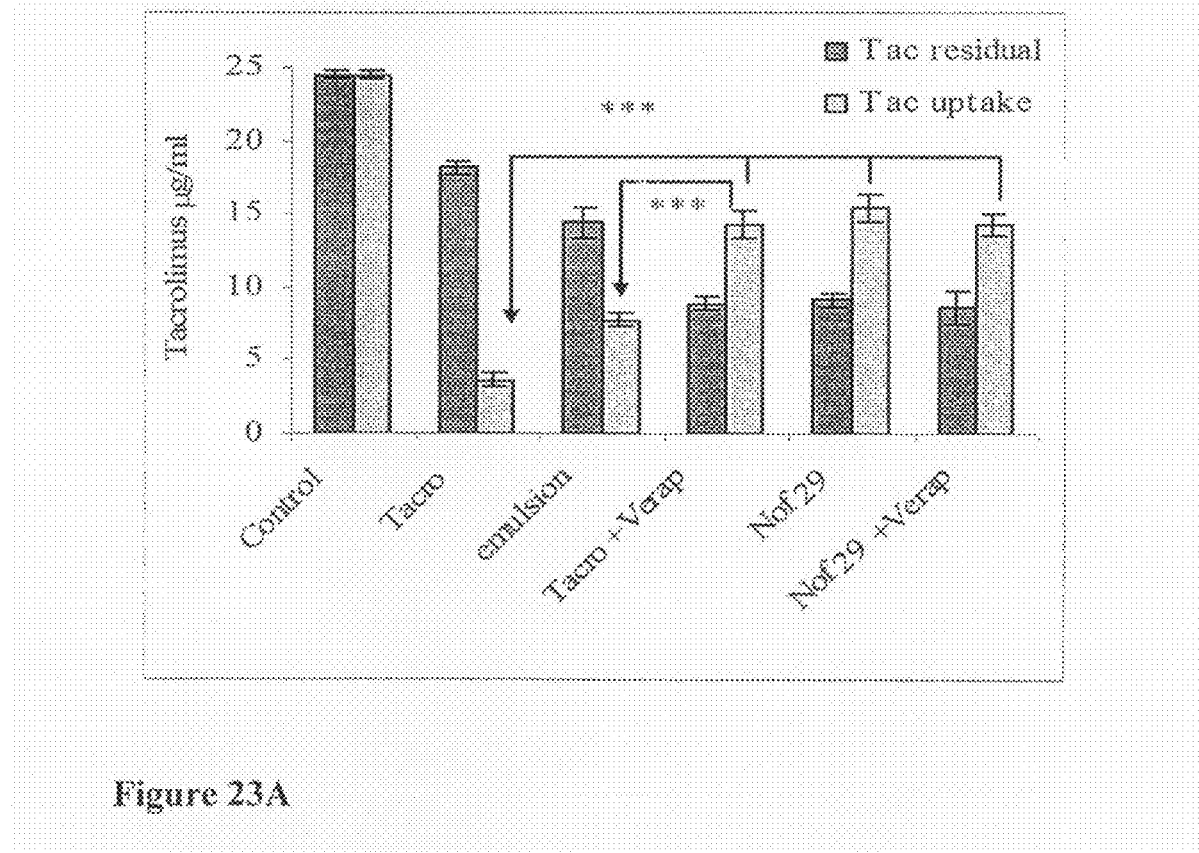
FIG. 23A-23B are graphs showing either tacrolimus residue in Hanks buffer (pH 7.4) following 60 min incubation in Caco-2 cell monolayer and respective tacrolimus uptake following washing and cell lysis (SDS 1%) of various formulations containing 25 µg/ml tacrolimus in Caco-2 cell monolayer.
Figure 23B:
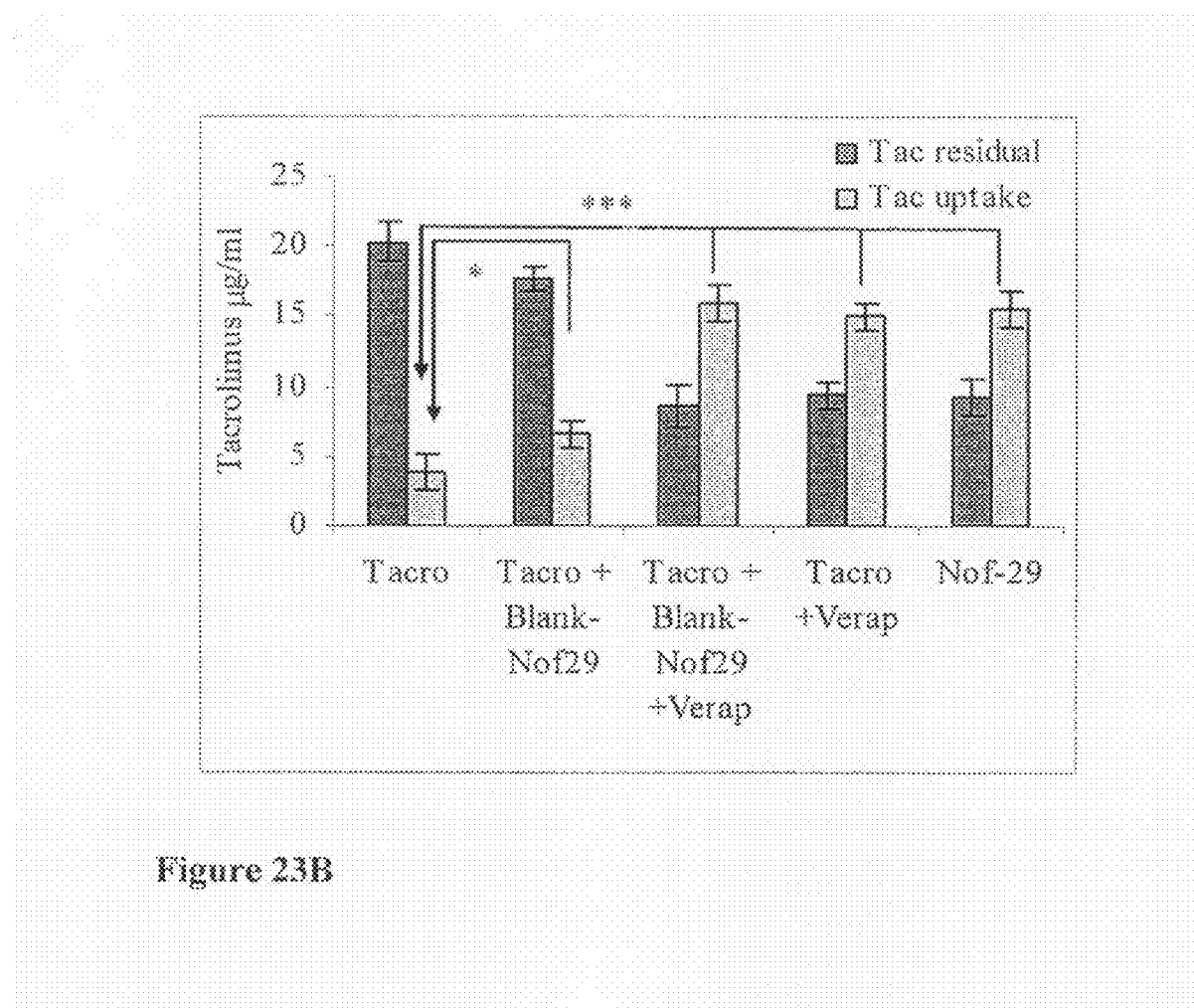

Tacrolimus residual concentration in the wells with no Caco-2 cells remained constant and diminished moderately in the presence of Caco-2 cells from the apical side when dissolved in Hanks buffer or in the argan oil/oleoyl polyoxylglycerides phase (FIG. 23A). The tacrolimus concentration decreased significantly in the presence of verapamil, a well-known P-gp inhibitor and CYP3A substrate (C. U. Wu and L. Z. Benet. Predicting drug disposition via application of BCS: transport/absorption/elimination interplay and development of a biopharmaceutics drug disposition classification system. *Pharm. Res.* 22: 11-23 (2005) showing a marked uptake by the Caco-2 cell monolayer. It should be emphasized that the concentration of tacrolimus from the novel DDS (Nof-29) was also low and adding verapamil to the Nof-29 formulation did not further decrease the concentration of tacrolimus (FIG. 23A). This was also confirmed by the data presented in FIG. 23B showing the respective tacrolimus uptake by the Caco-2 cell monolayer. The highest drug uptake was achieved by the tacrolimus solution combined with verapamil and Nof-29 either alone or in combination with verapamil, suggesting that verapamil had no effect on tacrolimus absorption elicited by Nof-29 formulation. Statistical analysis of the apparent permeability ($P_{app}$) values, indicated that there was no significant difference between the tacrolimus and verapamil formulation, Nof-29 formulation with and without verapamil (respective values of $8.07 \pm 0.50 \times 10^{-6}$, $8.71 \pm 0.53 \times 10^{-6}$ and $8.08 \pm 0.46 \times 10^{-6}$ cm/s). However, these $P_{app}$ values were significantly higher than the values yielded by the reconstituted emulsion ($4.4 \pm 0.24 \times 10^{-6}$ cm/s) and the tacrolimus aqueous solution ($2.05 \pm 0.26 \times 10^{-6}$ cm/s). Again, under the given experimental conditions, the emulsion could not retain the dissolved tacrolimus in the oil droplets and part of it partitioned in favor of the medium from where it could penetrate the Caco-2 cells and be effluxed as the normal tacrolimus dissolved in the aqueous solution. Furthermore, it can be noted from a second set of experiments, the data of which are depicted in FIG. 24, that the blank Nof-29 formulation in presence of tacrolimus solution, moderately enhanced the drug uptake as compared to tacrolimus solution alone. However, it was significantly less than tacrolimus solution containing verapamil with and without blank Nof-29 or tacrolimus loaded Nof-29 formulation clearly indicating that the blank DDS per se does not markedly affect the P-gp pump activity. The moderate increase in tacrolimus uptake can be attributed to the presence of numerous blank lipophilic oil cores that enhance the tacrolimus solubility in the aqueous environment. It could be deduced from the overall results of these experiments that the delivery system of the invention does not activate the P-gp since the pump does not recognize tacrolimus which is hidden in the coated oil cores of the nanocapsules.

Transport of Tacrolimus Across the Intestinal Membrane Via an In Vitro Diffusion Chamber System.

All the animal studies in this research were carried out in accordance with the rules and guidelines concerning the care and use of laboratory animals MD 104.01-3 and were approved by the local ethical committee of laboratory animal care at The Hebrew University of Jerusalem.

The tacrolimus across the rat intestinal membrane was studied with the Ussing diffusion chamber (Y. Gotoh, N. Kamada and D. Momose. The advantages of the Ussing chamber in drug absorption studies. *J. Biomol. Screen* 10: 517-23 (2005). Sprague Dawley rats, weighing 280-350 g, were fasted overnight and then anesthetized with sodium pentobarbital (30 mg/kg). The intestine jejunum was exposed through a midline abdominal incision, removed, and washed in ice-cold saline. Intestinal segments were isolated and immersed in ice-cold KRBS. Segments were cut open, the intestinal sheets were mounted onto the pins of the cells, and the half-cells were clamped together. Drug solutions and formulation (7 ml) were added to the donor site with an initial concentration of 25 µg/ml, whereas the same volume of drug-free buffer was added to the opposite site. The temperature of cells was maintained at 37° C., and both fluids were circulated by gas lift with 95% $O_2$/5% $CO_2$. When verapamil was used, the concentration in the medium was 150 µg/ml and the intestinal segments were pre-incubated with the verapamil solution 30 min prior to the permeation experiments. During the transport studies, aliquots were taken from the serosal side and the permeated tacrolimus was assayed by HPLC as described above. It should be mentioned that prior to the permeability studies, the serosa was removed from the jejunum segments. The experiments were quadruplicated.

The apparent permeability ($P_{app}$, cm/s) was calculated (P. Anderle, E. Niederer, W. Rubas, C. Hilgendorf, H. Spahn-Langguth, H. Wunderli-Allenspach, H. P. Merkle and P. Langguth. P-glycoprotein (P-gp) mediated efflux in Caco-2 cell monolayers: the influence of culturing conditions and drug exposure on P-gp expression levels. *J. Pharm. Sci.* 87: (6) 757-762 (1998).

Results

The permeation studies through the intestinal jejunum membrane should shed light on the combined role of P-gp efflux and Cytochrome P450 3A (CYP3A) as potential biochemical barriers to limit the passage of tacrolimus across the enterocytes since Caco-2 cells do not express specifically CYP3A that mainly metabolize tacrolimus. The results presented in FIG. 24, showing the passage from the apical to the basal side of the intestinal mucosa without serosa clearly support the results of the Caco-2 monolayer experiments. It can again be observed that both Prograf®, the commercial product and the argan oil/oleoyl polyoxylglycerides emulsion did not enhance the permeation through the intestine (respective $P_{app}$ values calculated from equation 3 of 209.3±17.7 and 179±38.9 $10^{-6}$ cm/s) because of the P-gp efflux and CYP450 enzymes. However, when tacrolimus reconstituted emulsion was combined with verapamil, tacrolimus permeation increased markedly as reflected by the $P_{app}$ values of 480.8±76.8 $10^{-6}$ cm/s but still significantly less than the $P_{app}$ value of 608.6±64.3 $10^{-6}$ cm/s yielded by Nof-29 (FIG. 24). The addition of verapamil to Nof-29 did not alter the absorption profile of tacrolimus ($P_{app}$ value of 533.7±21.7 $10^{-6}$ cm/s) confirming that tacrolimus absorption was not influenced by the presence of the potent P-gp inhibitor and CYP3A substrate. These data confirm that the emulsion was not able to retain the tacrolimus within the oil droplets under the actual experimental conditions mimicking physiological conditions. Thus, tacrolimus was subjected to the metabolism effect of the CYP enzymes and efflux pump effect of P-gp resulting in a low passage of the drug to the serosal side of the intestine (FIG. 24). However, when the tacrolimus emulsion was combined with verapamil, tacrolimus permeation increased markedly but still significantly less than with Nof-29 (FIG. 24). The $P_{app}$ values elicited by Nof-29 with and without verapamil did not differ. These data demonstrate and confirm again that the novel delivery system enhances the tacrolimus absorption by escaping the P-gp efflux pump effect and protecting the drug from the degradation effect of the CYP450 enzymes.

Fluorescent Histological Studies

Male Sprague Dawley rats (N=9) were used in this study. The animals were divided into three groups. Following overnight fasting conditions, the animals were dosed by oral gavage, of Nile red, a lipid fluorescent marker incorporated in the Control (saline), argan/labrafil oil phase and Nof-29 (1 mg/ml oil phase). Thirty minutes after dose administration the animals were sacrificed and a 10 cm segment of the jejunum was dissected and fixed in 4% neutrally buffered formalin for further histology analysis. The samples were prepared using cryostat sectioning. Images were taken using a Nikon TE-2000S (Nikon, Melville, N.Y.) inverted fluorescence microscope with a plan Apo 60× objective lens (Nikon) and a Hammamatsu CCD ORCAII camera (Hammamatsu, Tucson, Ariz.) in 488 nm excitation wavelength and 515 nm wavelength of emission. Images were all deconvolved with SimplePCI software (Improvision, Coventry, UK) and processed using Photoshop 7 software.

Results

The optical data depicted in FIG. 25A-25D show the lack of any fluorescence in the enterocytes of the jejunum 30 min after the oral administration of Nile red loaded saline or oil core phase while N of 29 formulation elicited the penetration of fluorescent lipophilic tiny droplets, presumably intact nanocapsules (FIG. 25A-25D). These histological results indicated that the orally administered N of 29 formulation was rapidly absorbed into the enterocytes lining the small intestine followed by the villar stromal cells engulfment. Due to the rapid absorption, it may be suggested that the administered nanocapsules penetrated un-hydrolyzed into the enterocytes. It can also be deduced from the data depicted in FIG. 25C-25D that once the microspheres reached the jejunum, where the pH is above 7, they swelled and adhered to the mucosa owing to the presence of HPMC while the EUDRAGIT L dissolved, creating large pores in the microsphere matrices. This allowed the diffusion of presumably intact Nile red loaded nanocapsules.

Statistical Tests

Differences were analyzed by One-way Analysis of Variance (ANOVA) for the Caco-2 monolayer and intestinal transport studies. The tests were applied to the curves and calculated parameters. Analysis was determined with the Tukey-Kramer multiple comparisons test calculated by InStat software (version 3.01). The level of significance was corrected using a post test analysis. Statistical significance was set with one * for p<0.05 and with *** for p<0.001 while values are presented as mean±S.D.

Example 4

Felodipine Formulations

Formulation 1: with PLA 10 000 as Nanocapsule Coating Polymer:

A delivery system comprising felodipine as the drug were prepared according to the procedure described in Example 1. The composition was obtained:

TABLE 10

Composition of Felodipine -nanocapsule formulation

| # | Material Name | Amount | Unit |
|---|---|---|---|
| 1 | Methocel E4M | 1 | g |
| 2 | EURAGIT L100-55 | 0.75 | g |
| 3 | Sodium phosphate | 0.115 | g |
| 4 | Oleic acid | 1.5 | g |
| 5 | Labrafil M 1944 CS | 0.1 | ml |
| 6 | PLA 10,000 | 0.1 | g |
| 7 | Felodipine | 0.09 | g |

Felodipine Content Determination:

The theoretical content was determined as described above to be 2.33% w/w.

Content determination was carried out using the RP HPLC method using the following conditions: Mobile phase—acetonitrile:DDW 60:40; Column: C18 250*4.0 mm, Flow rate: 1.5 ml/min, Wavelength: 254 nm, Retention time: 7.5 min. It was determined that a sample of 10 mg contained 163.2 µg Felodipine in other words, it was determined that the Felodipine was 1.63% w/w.

Particle Size of the Nanocapsules:

Particle radius measurements were carried out utilizing an ALV Non-Invasive Back Scattering High Performance Particle Sizer, at 25° C., concentration of 125 µg/ml.

Mean peak position: 292.9 nm

Weight of peak [%]: 99.468

Zeta potential (mV): measured at 25° C., attenuator 9: 18.8

Formulation 2: with PLA 60 000 as Nanocapsule Coating Polymer

A delivery system comprising felodipine as the drug were prepared according to the procedure described in Example 1. The composition was obtained

TABLE 11

Composition of Felodipine -nanocapsule formulation

| # | Material Name | Amount | Unit |
|---|---|---|---|
| 1 | Methocel E4M | 1 | g |
| 2 | EURAGIT L100-55 | 0.75 | g |
| 3 | Sodium phosphate | 0.115 | g |
| 4 | Oleic acid | 1.5 | g |
| 5 | Labrafil M 1944 CS | 0.3 | ml |
| 6 | PLA 60,000 | 0.1 | g |
| 7 | Felodipine | 0.09 | g |

Felodipine Content Determination:

Felodipine content determination was conducted as described with respect to Felodipine formulation 1. A sample of 10 mg contains 172.7.2 µg Felodipine, being 1.72% w/w.

Particle Size of the Nanocapsules:

Particle radius measurements were carried out as described with respect to Felodipine formulation 1.

Mean peak position: 160.9 nm

Weight of peak [%]: 100

Zeta potential (mV): −2.93

Example 6

Docetaxel Formulation with PLAs

Preparation of Nanocapsules

The primary nanocapsules were prepared by dissolving in a of 100 ml of acetone, the following compounds: 500 mg of Glyceryl tributyrate, 100 mg of oleoyl polyoxylglycerides (Labrafil M 1944 CS), 100 mg of polylactic acid (PLA) 10,000 or 60,000, and 60 mg docetaxel (Tables 11&12). Then, 70 ml of bi-distilled water were slowly added to the organic phase. To the dispersed solution, 5 mM sodium phosphate buffer with 750 mg of EUDRAGIT L at pH 6.5 and 100 ml of 1% HPMC solution were added. The suspension was diluted to 500 ml with bi-distilled water and was filtered through a gauze pad.

TABLE 12

| Formulation # | Amount | Unit |
|---|---|---|
| Table 12A: Composition of nanocapsule formulation (form1PLA10) | | |
| Acetone | 100 | ml |
| PLA 10,000 | 0.1 | g |
| Labrafil M 1944 CS | 0.1 | g |
| Glyceryl tributyrate | 0.5 | g |
| Docetaxel | 60 | mg |
| DD water | 70 | ml |
| HPMC | 1 | g |
| DD water | 100 | ml |
| Sodium phosphate buffer | 5 | mM |
| EURAGIT L 100-55 | 0.75 | g |
| NaOH sol. 1N sufficient to obtain pH 6.5 | | |
| Table 12B: Composition of nanocapsule formulation (form2PLA60) | | |
| Acetone | 100 | ml |
| PLA 60,000 | 0.1 | g |
| Labrafil M 1944 CS | 0.1 | g |
| Glyceryl tributyrate | 0.5 | g |
| Docetaxel | 60 | mg |
| DD water | 70 | ml |
| HPMC | 1 | G |
| DD water | 100 | ml |
| Sodium phosphate buffer | 5 | mM |
| EURAGIT L 100-55 (Poly(methacyclic acid-co-ethyl)) 1:1) | 0.75 | G |
| NaOH sol. 1N sufficient to obtain pH 6.5 | | |

Microencapsulation of the Nanocapsules by Spray Drying Method:

The suspension was spray-dried with a Buchi mini spray-drier B-190 apparatus (Flawil, Switzerland) under the following conditions: inlet temperature 150° C.; outlet temperature 25° C.; aspiration 50%; feeding rate of the suspension was 2.5 ml/min. The powder was collected in the cyclone separator and the outlet yield was calculated.

form1PLA10: The collected powder was 383 mg.

form2PLA60: The collected powder was 300 mg.

Physicochemical Characterization of Drug Loaded Nanocapsules and Subsequent Microcapsules Drug Content The total amount of the drug in the final dried powder microspheres was determined by HPLC analysis following dissolution of 10.2 mg of the dried formulation in 3 ml of DMSO. The dispersion was stirred in an automatic shaker over 1 h up to complete dissolution of the powder. Thereafter, 2 ml of water and 4 ml of ethyl acetate were added and the mixture was stirred vigorously and centrifuged at 4000 rpm over 5 min. The extraction of docetaxel by ethyl acetate was repeated 3 times to ensure total removal of the drug from the bi-phasic solution. The different ethyl acetate layers (upper layer) were transferred to clean tube and evaporated under $N_2$ to dryness. The combined residues were dissolved in 1 ml of ACN, and 50 µl were injected into HPLC under the following conditions: mobile phase 60% ACN and 40% water, flow rate 0.6 ml/min, wavelength 230 nm, column LiChrospher® 100 RP-18 (5 µm) 4/125 mm. A calibration curve of docetaxel with concentrations ranging between 0.1 to 100 µg/ml yielded a linear correlation. The detection limit of docetaxel was found to be 0.25 µg/ml.

The docetaxel incorporation yield was calculated according to the equation provided in Example 1. Drug yield for form1PLA10(%)=(72.4 µg/233.14 µg)×100=31%

Drug yield for form2PLA60(%)=(226.985 µg/233.14 µg)×100=97.36%

Measurement of Particle Size by ALV:

Nanocapsule size measurements were carried out utilizing an ALV Non-Invasive Back Scattering High Performance Particle Sizer (ALV-NIBS HPPS; Langen, Germany) at 25° C. and using water as the solvent.

The radius ALV particle size of form1PLA10: 328 nm.

The radius ALV particle size of form2PLA60: 210 nm.

Measurement of Zeta Potential:

The zeta potential of form1PLA10: −15.3 mV.

The zeta potential of form2PLA60: −8.165 mV.

The invention claimed is:

1. A microsphere, comprising:
 a plurality of nanocapsules accommodated in a gel forming polymer, the plurality of nanocapsules each comprising
  a liquid oil core comprising a non-hydrophilic active agent dispersed or dissolved therein, and
  a shell of polymeric coating.

2. The microsphere of claim 1, wherein the polymeric coating comprises at least one polymer which is water insoluble or soluble at a pH above about 5.0, or a combination of same.

3. The microsphere of claim 2, wherein said polymeric coating comprises a combination of at least two polymers.

4. The microsphere of claim 3, wherein said combination of at least two polymers comprises at least one polymer which is soluble at a pH above about 5.0 and at least one polymer which is water insoluble.

5. The microsphere of claim 2, wherein said polymer which is soluble at a pH above about 5.0 is selected from hydroxypropylmethylcellulose phthalate (HPMPC), cellulose acetate phthalate, carboxy-methylcellulose phthalate, shellac, -poly(methacrylic acid-co-ethyl acrylate) 1:1, or zein.

6. The microsphere of claim 2, wherein the polymer which is a water insoluble polymer is selected from the group consisting of ethyl cellulose, Poly(ethyl acrylate-co-methyl methacrylate-co-trimethylammonioethyl methacrylate chloride) 1:2:0.1, Poly(ethyl acrylate-co-methyl methacrylate-co-trimethylammonioethyl methacrylate chloride) 1:2:0.2, polylactic acid (PLA), polyglycolic acid (PGA) and copolymers of PLA and PGA (PLAGA).

7. The microsphere of claim 3, wherein the combination of polymers comprises at least two polymers, a first polymer being water insoluble and a second polymer being soluble at a pH above about 5.0, the weight ratio between the water insoluble polymer and the polymer soluble at pH above about 5.0 being in the range between 5:95 and 70:30.

8. The microsphere of claim 3, wherein said combination of at least two polymers comprises a mixture of a first polymer selected from polylactic acid (PLA), poly(ethyl acrylate-co-methyl methacrylate-co-trimethylammonioethyl methacrylate chloride) 1:2:0.2 or poly(ethyl acrylate-co-methyl methacrylate-co-trimethylammonioethyl methacrylate chloride) 1:2:0.1 and a second polymer selected from poly(methacrylic acid-co-ethyl acrylate) 1:1 or hydroxypropyl methylcellulose phthalate (HPMPC).

9. The microsphere of claim 1, wherein the nanocapsules have an average diameter of between about 100 nm and 900 nm.

10. The microsphere of claim 1, wherein the gel forming polymer is a water soluble polymer or a polymer that swells in the presence of water.

11. The microsphere of claim 10, wherein the gel forming polymer is a modified cellulose selected from the group consisting of hydroxyethylcellulose, hydroxypropylmethylcellulose, sodium carboxymethyl cellulose, hydroxypropyl methyl cellulose phthalate, hydroxypropylmethylcellulose acetate succinate, cellulose acetate phthalate, methyl cellulose phthalate and microcrystalline cellulose.

12. The microsphere of claim 10, wherein the water soluble polymer is selected from the group consisting of hydroxypropyl methyl cellulose, methylcellulose and polyethylene glycol of molecular weight above 5000.

13. The microsphere of claim 1, wherein the microspheres have an average diameter of between about 5 µm to about 500 µm.

14. The microsphere of claim 1, wherein the active agent is a substrate of P-gp efflux pump.

15. The microsphere of claim 1, wherein the active agent is a lipophilic active agent or an amphipathic active agent.

16. A method of preparing microspheres comprising a plurality of nanocapsules accommodated in a gel-forming polymer, the plurality of nanocapsules each comprising a liquid oil core comprising a non-hydrophilic active agent dispersed or dissolved therein and a shell of polymeric coating, the method comprising:
 (a) providing an organic phase comprising oil, a water miscible organic solvent, a non-hydrophilic active agent dissolved in the solvent and a polymer or combination of polymers for coating said liquid oil core;
 (b) slowly adding water to said organic phase to obtain a water in oil (w/o) emulsion;
 (c) continuously adding water to the w/o emulsion to induce phase inversion of the emulsion thereby obtaining an oil in water (o/w) emulsion;
 (d) mixing said o/w emulsion with a gel forming polymer or a combination of gel forming polymers;
 (e) removing the organic solvent and water thereby obtaining said microspheres.

17. The method of claim 16, wherein said organic solvent is selected from ethanol, methanol, acetone, ethyl acetate, or isopropanol.

18. The method of claim 16, wherein said polymeric coating comprises at least one polymer which is water insoluble or soluble at a pH above about 5.0 or a combination of same.

19. The method of claim 16, wherein said polymeric coating comprises a combination of at least two polymers.

20. The method of claim 19, wherein said combination of at least two polymers comprises at least one polymer which is soluble at a pH above about 5.0 and at least one polymer which is water insoluble.

21. The method of claim 20, wherein said polymer which is soluble at a pH above about 5.0 is selected from: hydroxypropylmethylcellulose phthalate, cellulose acetate phthalate, carboxy-methylcellulose phthalate, shellac, poly(methacrylic acid-co-ethyl acrylate) 1:1, or zein.

22. The method of claim 20, wherein said polymer which is water insoluble is selected from ethyl cellulose, poly(ethyl acrylate-co-methyl methacrylate-co-trimethylammonioethyl methacrylate chloride) 1:2:0.1, poly(ethyl acrylate-co-methyl methacrylate-co-trimethylammonioethyl methacrylate chloride) 1:2:0.2, polylactic acid (PLA), polyglycolic acid (PGA) or copolymers of PLA and PGA (PLAGA).

23. The method of claim 18, wherein said organic phase comprises lipophilic excipients.

24. The method of claim 16, wherein said organic phase comprises a lipophilic surfactant.

25. The method of claim 16, wherein said gel forming polymer is characterized in that it is at least one of the following: a water soluble polymer; or a polymer that swells in the presence of water.

26. The method of claim 16, wherein removing of said organic solvent and water is obtainable by spray drying.

27. A pharmaceutical composition, comprising: a microsphere comprising
a plurality of nanocapsules accommodated in a gel-forming polymer, each nanocapsule comprising a liquid oil core comprising a non-hydrophilic active agent dispersed or dissolved therein, and a shell of polymeric coating.

28. The pharmaceutical composition of claim 27, in a dosage form for oral administration.

29. The pharmaceutical composition of claim 28, being a dry pharmaceutical composition.

30. The pharmaceutical composition of claim 28, for controlled release of the active agent from the microsphere.

31. A method of increasing bioavailability of a lipophilic agent in a human subject's body, the method comprising administering to said subject microspheres comprising a plurality of nanocapsules accommodated in a gel-forming polymer, each nanocapsule comprising a liquid oil core carrying a lipophilic agent and a shell of polymeric coating.

32. A method of treating a subject for a pathological condition which requires for said treatment an effective blood level of an active agent, the method comprising administering to said subject microspheres comprising a plurality of nanocapsules accommodated in a gel-forming polymer, each nanocapsule comprising a liquid oil core carrying a lipophilic agent and a shell of polymeric coating.

33. The pharmaceutical composition of claim 27, wherein the microsphere is configured to selectively release the non-hydrophilic active agent into systemic blood circulation.

34. A microsphere, comprising:
a plurality of nanocapsules each comprising
a liquid oil core,
a non-hydrophilic active agent dissolved or dispersed within the liquid oil core, and
a polymeric shell coating the liquid oil core containing the non-hydrophilic active agent, the polymeric shell comprising a combination of at least one water insoluble polymer and at least one polymer that is soluble at a pH above about 5.0; and
a gel-forming polymer accommodating the plurality of nanocapsules.

35. A microsphere, comprising:
a plurality of nanocapsules each comprising
a liquid oil core,
a non-hydrophilic active agent dissolved or dispersed within the liquid oil core, and
a polymeric shell coating the liquid oil core containing the non-hydrophilic active agent; and
a gel-forming polymer accommodating the plurality of nanocapsules,
wherein the microsphere is configured to selectively release the non-hydrophilic active agent into systemic blood circulation.

36. The microsphere of claim 35, wherein there is no direct contact between the non-hydrophilic active agent in the liquid oil core and the gel-forming polymer.

\* \* \* \* \*